(12) United States Patent
Zughaier et al.

(10) Patent No.: US 8,841,317 B2
(45) Date of Patent: Sep. 23, 2014

(54) NOSCAPINE AND ANALOGS AND METHODS RELATED THERETO

(75) Inventors: Susu Zughaier, Atlanta, GA (US); Ritu Aneja, Lilburn, GA (US); David S. Stephens, Stone Mountain, GA (US)

(73) Assignees: Emory University, Atlanta, GA (US); Georgia State University Research Foundation, Atlanta, GA (US)

( * ) Notice: Subject to any disclaimer, the term of this patent is extended or adjusted under 35 U.S.C. 154(b) by 39 days.

(21) Appl. No.: 13/216,458

(22) Filed: Aug. 24, 2011

(65) Prior Publication Data
US 2012/0053199 A1 Mar. 1, 2012

Related U.S. Application Data

(60) Provisional application No. 61/376,749, filed on Aug. 25, 2010.

(51) Int. Cl.
*A61K 31/44* (2006.01)
*A61K 31/4355* (2006.01)

(52) U.S. Cl.
CPC .................................. *A61K 31/4355* (2013.01)
USPC ......................................... 514/280; 514/291

(58) Field of Classification Search
USPC ................................................ 514/280, 291
See application file for complete search history.

(56) References Cited

U.S. PATENT DOCUMENTS

| 4,922,901 | A | 5/1990 | Brooks et al. |
| 2007/0243132 | A1 | 10/2007 | Russell-Jones et al. |
| 2009/0203763 | A1 | 8/2009 | Gant |

FOREIGN PATENT DOCUMENTS

| WO | 2008109609 A1 | 9/2008 |
| WO | 2010083104 A2 | 7/2010 |

OTHER PUBLICATIONS

Mahmoudian et al. "Anti-cancer Activity of Noscapine: A Review". Recent Patents on Anti-Cancer Drug Discovery, 2009, 4, 92-97.*
Aneja et al., (2006), "Drug-resistant T-lymphoid tumors undergo apoptosis selectively in response to an antimicrotubule agent, EM011.", Blood, 107(6): 2486-2492.
Aneja et al., (2006), "Synthesis of microtubule-interfering halogenated noscapine analogs that perturb mitosis in cancer cells followed by cell death", Biochem Pharmacol, 4 (72): 415-426.
Aneja et al., (2008), "Multidrug Resistance-Associated Protein—Overexpressing Teniposide-Resistant Human Lymphomas Undergo Apoptosis by a Tubulin-Binding Agent.", Cancer Res, 68(5): 1495-1503.
Aneja et al., (2010), "Non-toxic melanoma therapy by a novel tubulin-binding agent.", International Journal of Cancer, 126(1): 256-265.
Gupta et al., (2002), "Perturbation of Microtubule Polymerization by Quercetin through Tubulin Binding: A Novel Mechanism of Its Antiproliferative Activity", Biochem, 43 (41): 13023-13038.
Herman-Antosiewicz et al., (2006), "Sulforaphane Causes Autophagy to Inhibit Release of Cytochrome c and Apoptosis in Human Prostate Cancer Cells", Cancer Res, 11 (66): 5828-5835.
Karna et al., (2010), "Induction of reactive oxygen species-mediated autophagy by a novel microtubule-modulating agent.", J Biol Chem, 24 (285): 18737-18738.
Liu et al., (2010), "Osteoinductive LIM mineralization protein-1 suppresses activation of NF-kappaB and selectively regulates MAPK pathways in pre-osteoclasts.", Bone, 5 (46): 1328-1335.
Plant et al., (2006), "Lipooligosaccharide Structure Contributes to Multiple Steps in the Virulence of *Neisseria meningitidis*", Infect Immun, 2 (74): 1360-1367.
Prise et al., (1986), "Increased protein ADPribosylation in HeLa cells exposed to the anti-cancer drug methotrexate", Biochim Biophys Acta, 1 (887): 13-22.
Stephens et al., (2005), "Incidence of macrolide resistance in *Streptococcus pneumoniae* after introduction of the pneumococcal conjugate vaccine: population-based assessment", Lancet, 9462 (365): 855-863.
Tzeng et al., (2005), "Cationic Antimicrobial Peptide Resistance in *Neisseria meningitidis*", J Bacteriol, 15 (187): 5387-5396.
Williams et al., (2009), "Transmigration across activated endothelium induces transcriptional changes, inhibits apoptosis, and decreases antimicrobial protein expression in human monocytes.", Journal of Leukocyte Biology, 86(6): 1331-1343.
Zhou et al., (2003), "Brominated Derivatives of Noscapine Are Potent Microtubule-interfering Agents That Perturb Mitosis and Inhibit Cell Proliferation", Mol Pharmacol, 4 (63): 799-807.
Zughaier et al., (2010), "Potent anti-inflammatory activity of novel microtubule-modulating brominated noscapine analogs.", PLoS One, 2 (5): e9165.
Zughaier et al., (1999), "A Melanin Pigment Purified from an Epidemic Strain of *Burkholderia cepacia* Attenuates Monocyte Respiratory Burst Activity by Scavenging Superoxide Anion", Infect Immun, 2 (67): 908-913.
Zughaier et al., (1999), "Lipopolysaccharide (LPS) from *Burkholderia cepacia* Is More Active than LPS from *Pseudomonas aeruginosa* and *Stenotrophomonas maltophilia* in Stimulating Tumor Necrosis Factor Alpha from Human Monocytes", Infect Immun, 3 (67): 1505-1507.
Zughaier et al., (2004), "*Neisseria meningitidis* Lipooligosaccharide Structure-Dependent Activation of the Macrophage CD14/Toll-Like Receptor 4 Pathway", Infect Immun, 1 (72): 371-380.

(Continued)

*Primary Examiner* — Renee Claytor
(74) *Attorney, Agent, or Firm* — Emory Patent Group

(57) ABSTRACT

The invention relates to the innate immune pathway and anti-inflammatory molecules with therapeutic properties. In some embodiments, the invention relates to compounds and pharmaceutical compositions and methods of using the compounds and compositions to treat inflammatory diseases including inflammation associated with auto-immune diseases.

4 Claims, 6 Drawing Sheets

(56) References Cited

OTHER PUBLICATIONS

Zughaier et al., (2005), "Differential Induction of the Toll-Like Receptor 4-MyD88-Dependent and -Independent Signaling Pathways by Endotoxins", Infect Immun, 5 (73): 2940-2950.

Zughaier et al., (2006) "Antimicrobial peptides and endotoxin inhibit cytokine and nitric oxide release but amplify respiratory burst response in human and murine macrophages", Cell Microbiol, 9 (7): 1251-1262.

Zughaier et al., (2006), "Hexa-acylation and KDO2-glycosylation determine the specific immunostimulatory activity of *Neisseria meningitidis* lipid A for human monocyte derived dendritic cells", Vaccine, 9 (24): 1291-1297.

Zughaier et al., (2007), "Physicochemical characterization and biological activity of lipooligosaccharides and lipid A from *Neisseria meningitidis*", J Endotoxin Res, 6 (13): 343-357.

Zughaier et al., (2007), "TLR4-dependent adjuvant activity of *Neisseria meningitidis* lipid A.", Vaccine, 22 (25): 4401-4409.

Zughaier et al., (2010), "The human host defense peptide LL-37 interacts with *Neisseria meningitidis* capsular polysaccharides and inhibits inflammatory mediators release.", PLoS One, 10 (5): e13627.

Zughaier, S., (2011), "*Neisseria meningitidis* capsular polysaccharides induce inflammatory responses via TLR2 and TLR4-MD-2.", J Leukoc Biol, 3 (89): 469-480.

Karaiskos, J., (2011), "Defective macrophage function in crohn disease: role of alternatively activated macrophages in inflammation.", Gut, 60:A143-A144.

Van Deventer, SJ., (1997), "Tumor necrosis factor and Crohn's disease.", Gut 40(4): 443-448.

\* cited by examiner

NOSCAPINE AND ANALOGS AND METHODS RELATED THERETO

CROSS REFERENCE TO RELATED APPLICATIONS

This application claims priority to U.S. Provisional Application No. 61/376,749 filed the Aug. 25, 2010, hereby incorporated by reference.

This invention was made with government support under Grants K99-CA131489 awarded by the National Institutes of Health. The government has certain rights in the invention.

FIELD

The invention relates to the innate immune pathway and anti-inflammatory molecules with therapeutic properties. In some embodiments, the invention relates to compounds and pharmaceutical compositions and methods of using the compounds and compositions to treat inflammatory diseases including inflammation associated with auto-immune diseases.

BACKGROUND

The innate immune system plays a role in host defense and homeostasis Innate immune responses are induced when pattern recognition receptors such as Toll-like receptors (TLR) sense the presence of Pathogen Associated Molecular Patterns (PAMPs) or endogenous Damage Associated Molecular Patterns (DAMPs) released by damaged cells. Although acute innate pathway inflammatory responses promote termination of infection and wound healing, chronic activation of this pathway can lead to tissue damage and fibrosis and contribute to various disease states. Thus, there is a need to identify therapeutic strategies that prevent chronic activation of inflammatory pathways.

An estimated 46 million adults in the United States reported to have some form of arthritis, rheumatoid arthritis, gout, lupus, or fibromyalgia. Among them, atherosclerosis, arthritis and the IBD are the most common forms. Atherosclerosis (also known as arteriosclerotic vascular disease or ASVD) is a syndrome affecting arterial blood vessels, a chronic inflammatory response in the walls of arteries, in large part due to the accumulation of macrophage white blood cells and promoted by Low-density lipoproteins (plasma proteins that carry cholesterol and triglycerides) without adequate removal of fats and cholesterol from the macrophages by functional high density lipoproteins (HDL). Atherosclerosis is the usual cause of heart attacks, strokes, and peripheral vascular disease—together called "cardiovascular disease" and is the No. 1 killer in America, with more than 800,000 deaths in 2006. Arthritis is the most common cause of disability in the USA. More than 20 million individuals with arthritis have severe limitations in function on a daily basis. It is estimated that the total cost of arthritis cases is close to $100 billion of which nearly 50% accounts from lost earnings. Each year, arthritis results in nearly 1 million hospitalizations and close to 45 million outpatient visits to health care centers. Inflammatory Bowel Disease refers to two chronic diseases that cause inflammation of the intestines: ulcerative colitis and Crohn's disease. The prevalence rate for IBD is approx 1 in 500 or 0.20% or 544,000 people in the US.

Microtubule-disrupting agents are a new emerging class of anti-inflammatory agents. Microtubules are cytoskeletal structures responsible for maintaining genetic stability during cell division. The dynamics of these polymers can be described by their growth rate at the plus ends, catastrophic shortening, frequency of transition between the two phases, pause between the two phases, their release from the microtubule organizing centers and treadmilling. Microtubule lattice also serves as tracks for the axonal transport of organelles driven by ante-rograde and retrograde molecular motors to generate and maintain axonal integrity. Colchicine and vinblastine are examples of microtubule-disrupting agents that have been used as a class of anti-inflammatory agents. These agents have been shown to reduce TNFα production in macrophages due to their ability to impair tubulin dynamics. In particular, colchicine, a microtubule-depolymerizing agent, has been employed for gout management. However, toxicities limit colchicine's usefulness. Another tubulin inhibitor, vinblastine, used in the treatment of hematological malignancies, has significant toxic side-effects such as leucocytopenias, gastrointestinal toxicity, peripheral neuropathy, and immunosuppression. Interference with microtubule dynamics often leads to programmed cell death, thus, microtubule-binding drugs are currently used to treat various malignancies in the clinic.

The pharmacological profile of microtubule-binding agents has not been ideal. Most of them (i.e. taxanes) need to be infused over long periods of time in the clinic because they are not water-soluble, and can cause hypersensitive reactions due to the vehicle solution. Furthermore, normally dividing cells within the healthy tissues such as intestinal crypts, hair follicles, and the bone marrow are also vulnerable to these agents, leading to toxicities. In addition, nerve cells dependent on molecular traffic over long distances undergo degenerative changes causing peripheral neuropathies. Currently used microtubule drugs, such as vincas and taxanes, are also limited due to the emergence of drug resistance. There have been multiple mechanisms for anti-microtubule drug resistance including over expression of drug-efflux pumps, mis-expression of tubulin isotypes, and perhaps mutational lesions in tubulin itself. It would be desirable to have compounds, compositions and methods for preventing and/or treating various types of innate immune diseases, without significant associated toxicity, that provide increased anti-inflammatory properties to that of microtubule-disrupting agents and other anti-inflammatory agents.

SUMMARY

The invention relates to the innate immune pathway and anti-inflammatory molecules with therapeutic properties. In some embodiments, the invention relates to compounds and compositions and methods of using the compounds and compositions to treat inflammatory diseases including inflammation due to auto-immune diseases.

In some embodiments, the invention relates to compounds comprising Formula A:

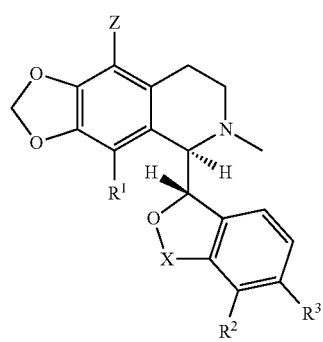

Formula A or pharmaceutically acceptable salts, prodrugs or derivatives thereof.

wherein Z is a halogen, nitro, or nitrogen wherein nitrogen may be optionally substituted with $R^4$; X is methylene ($CH_2$) optionally substituted with $R^4$; $R^1$, $R^2$, and $R^3$ are each independently an alkoxy optionally substituted with one or more $R^4$; $R^4$ is independently selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^4$ is optionally substituted with $R^5$;

$R^5$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl. In a typical embodiment, $R^1$, $R^2$, and $R^3$ are each methoxy.

In some embodiments, the invention relates to compounds of Formula A, pharmaceutical compositions, and methods of preparation, wherein Z is individually, selected any of the following: an alkyl group, an alkenyl group, a heterocyclic group, a cycloalkyl group, an aryl group, a heteroaryl group, an alkoxy group, an amine, a cyano group, a thiophenyl group, an azide group, an amide group, a carbonyl group, an ester group, an acetate group, a sulphonate group, a sulphonamide group or a halogen, any of which may be optionally substituted. The group X can be either a methylene ($CH_2$) group or a carbonyl (C=O) group and $R^1$, $R^2$, and $R^3$ are each independently an alkoxy.

In some embodiments the invention relates to a pharmaceutical composition comprising an excipient and a compound of formula A: or a pharmaceutically acceptable salt thereof, wherein Z is a halogen, nitro, or nitrogen wherein nitrogen may be substituted; X is methylene ($CH_2$); and $R^1$, $R^2$, and $R^3$ are each independently an alkoxy. In a typical embodiment, $R^1$, $R^2$, and $R^3$ are each methoxy.

In certain embodiments, Z is hydrogen, X is methylene ($CH_2$) or a carbonyl (C=O) group optionally substituted with $R^4$; $R^1$, $R^2$, and $R^3$ are each independently an alkoxy optionally substituted with one or more $R^4$.

In some embodiments, the invention relates to a method of treating an inflammation comprising administering to a subject diagnosed with, exhibiting symptoms, or at risk for an inflammation, a pharmaceutical composition compound of formula A. In certain embodiments, the subject is suffering from or at risk of a chronic innate immune system based inflammation.

In some embodiments, the invention relates to the use of a compound as provided Formula A in the production of a medicament for the treatment of inflammation.

In some embodiments, the invention relates to compounds, methods of preparation thereof and methods for treatment of inflammatory diseases, including, but not limited to, atherosclerosis, arthritis, and inflammatory bowel disease. It is a further object of the invention to provide compounds and methods of treatment or prophylaxis of other immune pathway diseases, and in particular cardiovascular diseases and neurodegenerative disorders.

The present invention provides compounds, pharmaceutical compositions including the compounds, and methods of preparation and use thereof including compounds of Formula A for the treatment of a host with diseases caused by innate immune disorder and for the treatment of inflammatory diseases.

In a further embodiment compounds, pharmaceutical compositions including the compounds, including compounds of Formula A or pharmaceutically acceptable salts, prodrugs or derivatives thereof significantly inhibit TNFα, IL-8 and nitric oxide release upon challenge with various TLR and non-TLR ligands mimicking septic and sterile innate immune pathways.

Within another aspect, the invention provides a method for treating inflammation, comprising administering a therapeutically sufficient amount of a noscapine analogue to a mammal, wherein the inflammation is acute. Within another aspect, the invention provides a method for treating inflammation, comprising administering a therapeutically sufficient amount of a noscapine analogue to a mammal, wherein the inflammation is chronic.

Within another aspect, the invention provides a method for treating inflammation, comprising administering a therapeutically sufficient amount of a noscapine analogue to a mammal, wherein the inflammatory condition of the mammal is associated with an autoimmune disease. In a more specific embodiment the noscapine analogue is brominated at the 9 position. The disclosed combination, alternation, or salvage regiments are useful in the prevention and treatment of and other related conditions such as Alzheimer's disease, arthritis, asthma, atherosclerosis, Crohn's disease, colitis, dermatitis, diverticulitis, hepatitis, irritable bowel syndrome (IBS), inflammatory bowel disease (IBD), lupus erythematous, nephritis, and Parkinson's disease.

In certain embodiments, the disclosure contemplates the use of the noscapine analogs for methods disclosed herein wherein the noscapine analog is a conjugate of noscapine and folic acid.

In certain embodiments, the disclosure contemplates the use of noscapine and noscapine analogs for the treatment or prevention of gout.

The foregoing and other aspects of the present invention are explained in detail in the detailed description and examples set forth below. Other compositions, methods, features, and advantages of the present disclosure will be or become apparent to one with skill in the art upon examination of the following drawings and detailed description. It is intended that all such additional compositions, methods, features, and advantages be included within this description, be within the scope of the present disclosure, and be protected by the accompanying claims.

TERMS

Figure 1:
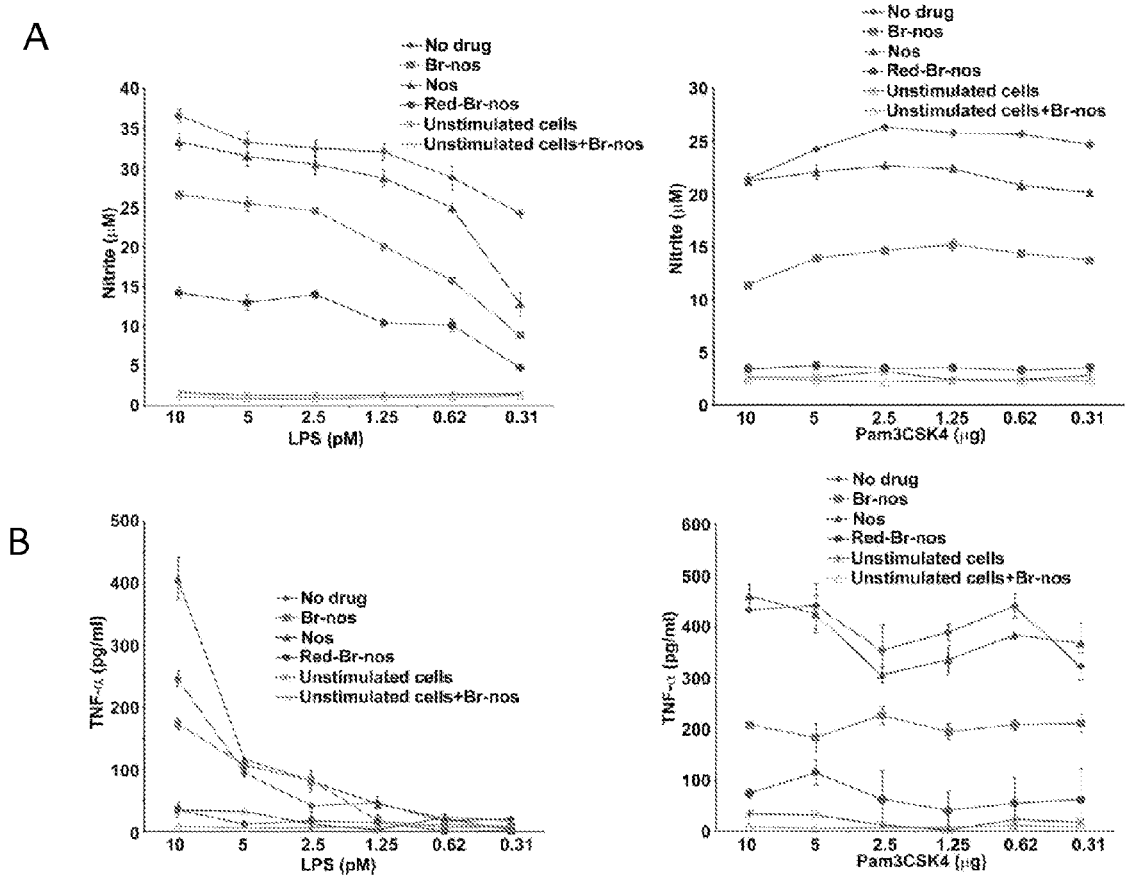
FIG. 1 illustrates pre-treatment of murine and human macrophages with noscapine analogs significantly inhibit TLR4 and TLR2 pathway inflammatory responses. Murine RAW 264.7 and human THP-1 macrophages were treated with 50 µM of noscapine analogs for 4 hrs followed by LPS induction in concentrations ranging from 10-0.31 pM, or Pam3CSK4 in concentrations ranging from 10-0.31 µg/ml overnight. A—Nitric oxide (NO) release was determined as nitrite accumulation in supernatants detected by the Griess method. B-TNFα release into supernatants was measured by ELISA. No drug: RAW264.7 cells treated with DMSO (50 µM) alone followed by LPS or Pam3CSK4 induction. Nos: noscapine followed by the TLR ligand (nitric oxide p value for LPS=0.0016, Pam3CSK4=0.00013 and TNFα p value for LPS=0.002, Pam3CSK4=0.1). Br-nos: 9-bromonoscapine followed by the TLR ligand (p value<0.00001). Red-Br-nos: Reduced bromonoscapine and the TLR ligand (p value<0.0001). Unstimulated cells were used as control and these cells were treated either with DMSO only or Br-nos (50 μM) without the TLR ligand. Error bars represent SD from mean of at least duplicate readings. Data are representative of at least 3 independent experiments. p values were calculated with reference to no drug values.

To facilitate understanding of embodiments of the invention, a number of terms are defined below.

The term "anti-inflammatory activity" as used herein refers to a 5%, 10%, 25%, 50%, 75%, 90%, or 100% decrease in the ability of noscapine and noscapine analogs to inhibit TLR4 and TLR2 pathway inflammatory responses, measured in any cell, tissue, or extract, relative to untreated control samples. This also refers to the bioavailability of noscapine and noscapine analogs in treated cells, tissues, or extracts, relative to untreated control samples. An example assay is provide below in the experimental section entitled "Cellular Activation and Inflammatory Responses."

The term "therapeutically effective amount" as used herein refers to that amount of the compound being administered which will relieve to some extent one or more of the symptoms of the disorder being treated. In reference to cancer or pathologies related to increased cell division, a therapeutically effective amount refers to that amount which has the effect of (1) reducing the TNFα, IL-8 and nitric oxide release, (2) inhibiting (that is, slowing to some extent, preferably stopping) septic and sterile innate immune response, (3) relieving to some extent (or, preferably, eliminating) one or more symptoms associated with a pathology related to or caused in part by inflammation, and/or (4) to prevent the chain of events downstream of inflammation which leads to the pathology.

"Pharmaceutically acceptable salt" refers to those salts which retain the biological effectiveness and properties of the free bases and which are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

A "pharmaceutical composition" refers to a mixture of one or more of the compounds described herein, or pharmaceutically acceptable salts thereof, with other chemical components, such as physiologically acceptable carriers and excipients. One purpose of a pharmaceutical composition is to facilitate administration of a compound to an organism.

As used herein, a "pharmaceutically acceptable carrier" refers to a carrier or diluent that does not cause significant irritation to an organism and does not abrogate the biological activity and properties of the administered compound.

An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

As used herein, the terms "prevent" and "preventing" include the prevention of the recurrence, spread or onset. It is not intended that the present invention be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present invention also contemplate treatment that merely reduces symptoms, and/or delays disease progression.

The term "alkyl" refers to straight or branched chain hydrocarbon groups having 1 to 12 carbon atoms, preferably 1 to 8 carbon atoms, such as methyl, ethyl, n-propyl, i-propyl, n-butyl, i-butyl, t-butyl, pentyl, hexyl, heptyl, octyl, and the like. The term "substituted alkyl" refers to alkyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), and the like.

The term "alkoxy" means an alkyl group linked to oxygen thus: R—O—. In this function, R represents the alkyl group. An example would be the methoxy group $CH_3O$—. The term "alkenyl" refers to straight or branched chain hydrocarbon groups having 2 to 12 carbon atoms, and at least one double carbon to carbon bond (either cis or trans), such as ethenyl. The term "substituted alkenyl" refers to alkenyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), and the like. The term "alkynyl" refers to straight or branched chain hydrocarbon groups having 2 to 12 carbon atoms, and at least one triple carbon to carbon bond, such as ethynyl. The term "substituted alkynyl" refers to alkynyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), and the like.

The terms "cycloalkyl" and "cycloalkenyl" refer to mono-, bi-, or tri homocyclic ring groups of 3 to 15 carbon atoms which are, respectively, fully saturated and partially unsaturated.

The term "cycloalkenyl" includes bi- and tricyclic ring systems that are not aromatic as a whole, but contain aromatic portions (e.g., fluorene, tetrahydronapthalene, dihydroindene, and the like). The rings of multi-ring cycloalkyl groups may be either fused, bridged and/or joined through one or more spiro unions. The terms "substituted cycloalkyl" and "substituted cycloalkenyl" refer, respectively, to cycloalkyl and cycloalkenyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), and the like. The terms "carbocyclo", "carbocyclic" or "carbocyclic group" refer to both cycloalkyl and cycloalkenyl groups. The terms "substituted carbocyclo", "substituted carbocyclic" or "substituted carbocyclic group" refer to carbocyclo or carbocyclic groups substituted with one or more groups as described in the definition of cycloalkyl and cycloalkenyl.

"Heterocarbocycles" or heterocarbocyclyl" groups are carbocycles which contain from 1 to 4 heteroatoms independently selected from nitrogen, oxygen and sulfur which may be saturated or unsaturated, including ring systems that are not aromatic as a whole, but contain aromatic portions, monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "aryl" refers to aromatic homocyclic (i.e., hydrocarbon) mono-, bi- or tricyclic ring-containing groups preferably having 6 to 12 members such as phenyl, naphthyl and biphenyl. Phenyl is a preferred aryl group. The term "substituted aryl" refers to aryl groups substituted with one or more groups, preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, and, the like, where optionally one or more pair of substituents together with the atoms to which they are bonded form a 3 to 7 member ring.

As used herein, "heteroaryl" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above with the indicated number of carbon atoms attached through a sulfur bridge. An example of an alkylthio is methylthio, (i.e., —S—CH3).

"Alkanoyl" refers to an alkyl as defined above with the indicated number of carbon atoms attached through a carbonyl bride (i.e., —(C=O)alkyl).

"Alkylsulfonyl" refers to an alkyl as defined above with the indicated number of carbon atoms attached through a sulfonyl bridge (i.e., —S(=O)2alkyl) such as mesyl and the like, and "Arylsulfonyl" refers to an aryl attached through a sulfonyl bridge (i.e., —S(=O)2aryl).

"Alkylsulfamoyl" refers to an alkyl as defined above with the indicated number of carbon atoms attached through a sulfamoyl bridge (i.e., —NHS(=O)2alkyl), and an "Arylsulfamoyl" refers to an alkyl attached through a sulfamoyl bridge (i.e., (i.e., —NHS(=O)2aryl).

"Alkylsulfinyl" refers to an alkyl as defined above with the indicated number of carbon atoms attached through a sulfinyl bridge (i.e. —S(=O)alkyl).

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO2Rb, —C(=O)Ra, —C(=O)ORa, —C(=O)NRaRb, —OC(=O)NRaRb, —ORa, —SRa, —SORa, —S(=O)2Ra, —OS(=O)2Ra and —S(=O)2ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

The terms "halogen" and "halo" refer to fluorine, chlorine, bromine, and iodine.

The term "aroyl" refers to an aryl group (which may be optionally substituted as described above) linked to a carbonyl group (e.g., —C(O)-aryl).

The terms "including", "such as", "for example" and the like are intended to refer to exemplary embodiments and not to limit the scope of the present disclosure.

DETAILED DISCUSSION

Noscapinoids constitute emerging class of small-molecule microtubule-modulating agents. The parent molecule, noscapine ((S)-6,7-dimethoxy-3-((R)-4-methoxy-6-methyl-5,6,7,8-tetrahydro[1,3]-dioxolo-[4,5-g]isoquinolin-5-yl) isobenzo-furan-1(3H)-one) binds tubulin, arrests dividing cells in mitosis and induces apoptosis. It is well tolerated in humans and has been shown to be non-toxic in healthy volunteers, including pregnant mothers. Unlike the other microtubule-targeting drugs, noscapine does not significantly change the microtubule polymer mass even at high concentrations. Instead, it suppresses microtubule dynamics by increasing the time that microtubules spend in an attenuated (pause) state when neither microtubule growth nor shortening is detectable. Thus, noscapine-induced suppression of microtubule dynamics, even though subtle, is sufficient to interfere with the proper attachment of chromosomes to kinetochore microtubules and to suppress the tension across paired kinetochores.

Brominated noscapine derivatives [(S)-3-((R)-9-bromo-4-methoxy-6-methyl-5,6,7,8-tetrahydro-[1,3]dioxolo[4,5-g] isoquinolin-5-yl)-6,7-dimethoxyiso-benzofuran-1(3H)-one, referred to as 9-bromonoscapine or Br-nos] and [(R)-9-bromo-5-((S)-4,5-dimethoxy-1,3-dihydroisobenzofuran-1-yl)-4-methoxy-6-methyl-5,6,7,8-tetrahydro-[1,3]di-oxolo-[4,5-g]isoquinoline, referred to as reduced-9-bromonoscapine or Red-Br-nos] have been shown to have significant anticancer activity and are non-toxic at doses as high as 300 mg/kg. Perhaps due to limited effects on microtubule dynamics, noscapine does not perturb the transport functions of microtubules in a variety of cell types such as post-mitotic neurons and has no apparent histo-, hemato-, immuno- or neuronal toxicity.

Published patent application WO 2008/109609 A1 (PCT/US2008/055811) provides for the use of noscapine analogs to treat cancers. US patent application 20070243132 A1 describes noscapine as an analgesic agent. US patent application 20090203763 describes noscapine as an antitussive agent.

Disclosed herein are investigations of the innate immune pathway as it relates to anti-inflammatory activity of noscapine and disclosed analogs. Our findings indicate that noscapine analogs have potent anti-inflammatory activity in septic and sterile inflammation models, in a dose-dependent and time-dependent manner. Brominated noscapine analogs (Br-nos and Red-Br-nos) dampened TLR-mediated TNF-α and nitric oxide (NO) release in human and murine macrophages without evidence of cellular toxicity. The analogs also inhibited cytokine/chemokine (a non-TLR ligand) induced inflammation that mimics sterile inflammation. These data suggest that the anti-inflammatory activity of the analogs is not due to a direct inhibition of TLR-receptor dimerization and signal initiation.

Two major classes of tubulin-binding drugs are taxanes (such as taxol, taxotere) and vincas (vinblastine, vincristine). While taxanes overpolymerize and bundle microtubules into sheets, vinca alkaloids depolymerize microtubules into soluble tubulin. Owing to their extreme effects on microtubules, both these classes of drugs interfere with microtubular-track dependent trafficking and cause toxicities such as peripheral neuropathies, gastrointestinal toxicity and immunosuppression. Unlike taxanes and vincas, for certain embodiments disclosed herein the analogs subtly attenuate microtubule dynamics and do not alter the monomer/polymer ratio of tubulin, which results in non-toxic properties. Brominated noscapine (EM011) modulates microtubule dynamics by increasing the 'pause' time of microtubules without affecting their overall existence. Aneja et al. (2010) Int J Cancer 126(1):256-65. Thus, noscapine analogs have been shown to be non-toxic with 'kinder and gentler' effects on microtubules. Interestingly, they possess potent anti-inflammatory activity and drug-induced attenuation of microtubule dynamics providing a possible mechanism contributing to dissipating cytosolic signaling thus dampening inflammatory responses.

Certain noscapine analogs when added to macrophages significantly induced autophagy as evident by extensive autophagy-related vacuolation in cytoplasm and upregulation of microtubule-associated light-chain protein, LC3-II, which integrates into the autophagic vesicles. Further, the inhibition of autophagy with 3-MA led to reduced anti-inflammatory activity. Thus, these data suggest that induction of autophagy is in part mediating the anti-inflammatory activity. Autophagy is a well-recognized conserved cellular pathway that removes macromolecules, recycles and degrades unwanted cytoplasmic components. The autophagosome fuses with the lytic lysosome to form autophagolysosomes that degrades engulfed molecules. Recently, the role of autophagy in host defense has become evident. TLRs are the environmental sensors for autophagy associated with innate immunity. Several recent reports demonstrate that autophagy, a bulk degradation system, is directly involved in the control of inflammatory immune responses. Genetic deficiency of Atg16L1, an autophagy protein, results in amplified inflammatory responses upon TLR stimulation as demonstrated by increased IL-1β release. Thus, as a component of the autophagic machinery, Atg16L1, suppresses endotoxin-induced intestinal inflammation. Autophagy might play a role in preventing or controlling inflammation. Thus, the cross-talk between drug-induced and TLR-mediated autophagic responses might impact inflammatory responses.

Oxidative and respiratory burst are cellular functions that play a role in homeostasis and host defense. Oxidative burst leads to the release of highly reactive oxygen species (ROS) radicals. Respiratory burst can be triggered by phagocytosis, drugs and toxins as well as by soluble stimulus like the protein kinase C activator PMA. ROS contribute to host defense by killing the invading pathogen and also act as a second messenger that induce release of chemokines and cytokines Host cationic peptides inhibit cytokine release from macrophages primed with endotoxin but enhanced ROS release. Although the underlying mechanism for ROS amplification is not clear, these peptides seem to exert catalytic effect on NADPH oxidases, xanthine oxidase and cytochrome c. Noscapine and certain analogs enhanced ROS release in LPS primed human macrophage cells but not in unprimed macrophages when added just prior to triggering the respiratory burst. The increase in ROS release may be due to the decline of mitochondrial transmembrane potential. One of the triggers for mitochondrial mediated apoptosis is the production of ROS.

ROS also play a role in induction of autophagy. The functional relationship between apoptosis ('self-killing') and autophagy ('self-eating') is intricate and complex in the sense that, under certain situations, autophagy constitutes a stress adaptation that avoids cell death (and suppresses apoptosis), whereas in other extreme cellular scenarios, it represents an alternative cell-death pathway.

Figure 8:
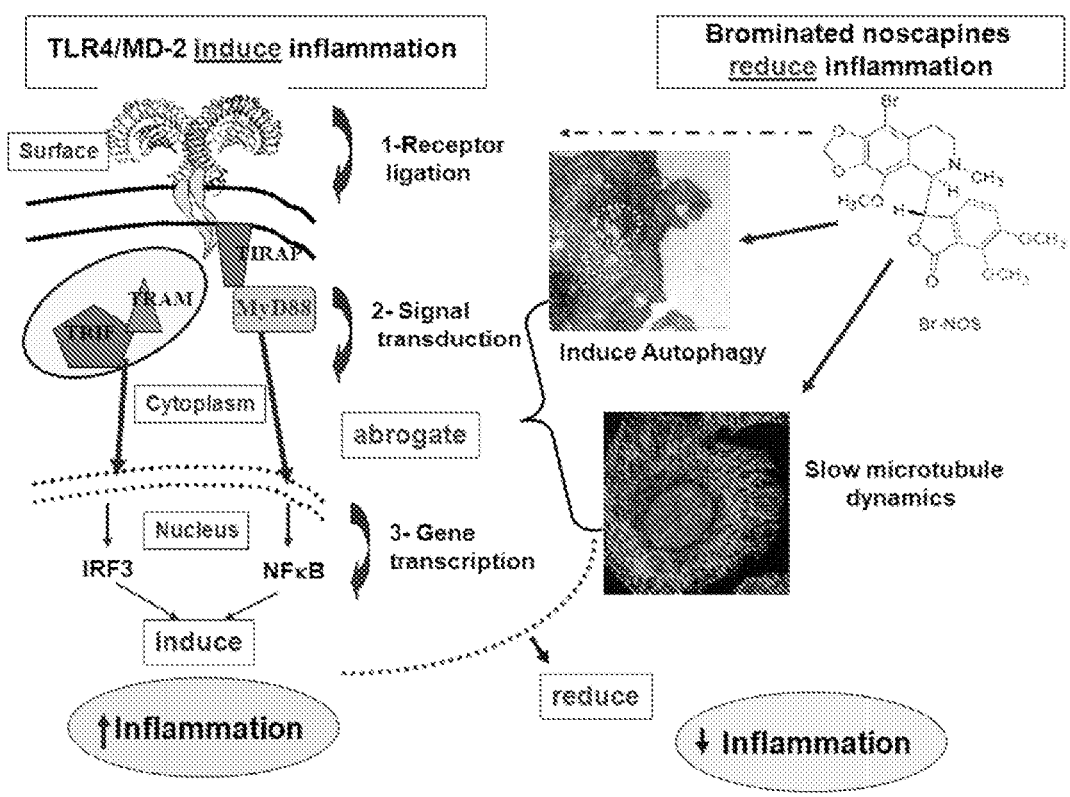
FIG. 8 illustrates TLR4/MD-2 induced inflammation and hypothetical mode of action for the drug induced anti-inflammatory effect. Theoretically, noscapine analogs may exert anti-inflammatory effect by interfering with targets either at 1—cell surface receptor ligation, 2—abrogating signal transduction by attenuating microtubule dynamics and/or by inducing autophagy, 3—inhibiting gene transcription in the nucleus.

Certain noscapine analogs display innate anti-inflammatory activity without affecting cell viability. Data suggests that certain non-toxic noscapine analogs may inhibit the pro-inflammatory responses by inducing autophagy that dampens inflammation by attenuating or recycling the inflammatory signaling complex. These analogs attenuate microtubule dynamics without altering the monomer/polymer ratio of tubulin. Thus, the anti-inflammatory effect may be due to a direct affect on tubulin and the associated slow dynamics might consequently dampen signal transduction or delay/impede protein transcription. Although it is not intended that embodiments of the invention disclosed herein be limited to any particular mechanism, FIG. 8 illustrates a proposed mechanism for anti-inflammatory mode of action in a schematic model.

The present disclosure may be understood more readily by reference to the following detailed description and the examples included therein. Before the present compounds, pharmaceutical compositions and methods of preparation and use are disclosed and described, it is to be understood that this disclosure is not limited to specific pharmaceutical carriers, or to particular pharmaceutical formulations or administration regimens, as such may, of course, vary. It is also to be understood that the terminology used herein is for the purpose of describing particular embodiments only and is not intended to be limiting.

Compounds, pharmaceutical compositions including the compounds, and methods of preparation and use thereof including compounds of Formula A or pharmaceutically acceptable salts, prodrugs or derivatives thereof, wherein are disclosed.

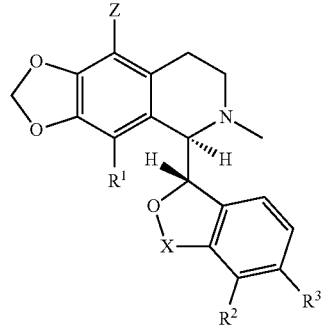

Formula A

In some embodiments, Z is a halogen, nitro, or nitrogen wherein nitrogen may be optionally substituted with $R^4$; X is methylene ($CH_2$) optionally substituted with $R^4$; $R^1$, $R^2$, and $R^3$ are each independently an alkoxy optionally substituted with one or more $R^4$; $R^4$ is independently selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^4$ is optionally substituted with $R^5$;

$R^5$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

In certain embodiments, Z is hydrogen. Typically X is methylene ($CH_2$) or a carbonyl (C=O) group optionally substituted with $R^4$. $R^1$, $R^2$, and $R^3$ are each independently an alkoxy optionally substituted with one or more $R^4$.

In some embodiments, the invention relates to compounds of Formula A, pharmaceutical compositions, and methods of preparation, wherein Z is individually, selected any of the following: an alkyl group, an alkenyl group, a heterocyclic group, a cycloalkyl group, an aryl group, a heteroaryl group, an alkoxy group, an amine, a cyano group, a thiophenyl group, an azide group, an amide group, a carbonyl group, an ester group, an acetate group, a sulphonate group, a sulphonamide group or a halogen, any of which may be optionally substituted. The group X can be either a methylene ($CH_2$) group or a carbonyl (C=O) group and $R^1$, $R^2$, and $R^3$ are each independently an alkoxy.

In some embodiments the invention relates to a pharmaceutical composition comprising an excipient and a compound of formula A: or a pharmaceutically acceptable salt thereof, wherein Z is a halogen, nitro, or nitrogen wherein nitrogen may be substituted; X is methylene ($CH_2$); and $R^1$, $R^2$, and $R^3$ are each independently an alkoxy. In a typical embodiment, $R^1$, $R^2$, and $R^3$ are each methoxy.

In some embodiments, Z is individually, selected any of the following: an alkyl group, an alkenyl group, a heterocyclic group, a cycloalkyl group, an aryl group, a heteroaryl group, an alkoxy group, an amine, a cyano group, a thiophenyl group, an azide group, an amide group, a carbonyl group, an ester group, an acetate group, a sulphonate group, a sulphonamide group or a halogen, any of which may be optionally substituted.

In some embodiments, $R^1$, $R^2$, and $R^3$ are each a $C_1$-$C_4$alkoxy. In a typical embodiment, $R^1$, $R^2$, and $R^3$ are each methoxy.

In some embodiments, X is a methylene (CH2) group. In other embodiments, X is a carbonyl (C=O) group.

In some embodiments, Z is selected from hydrogen, an alkyl group, an amine, an amide group, a carbonyl group, an ester group or a halogen, any of which may be optionally substituted. In more specific embodiments, Z is hydrogen, an amine or a halogen.

In more specific embodiments, the compounds are halogenated noscapine analogs, i.e. Z is a halogen, particularly a bromine, prodrugs or metabolites of these compounds, and pharmaceutically acceptable salts thereof. The compounds of both formulas can occur in varying degrees of enantiomeric excess.

Throughout the specification, groups and substituents thereof may be chosen to provide stable moieties and compounds.

To the extent that the disclosed compounds, and salts thereof, may exist in their tautomeric form, all such tautomeric forms are contemplated herein as part of the present disclosure.

The compounds can be in a free base form or in a salt form (e.g., as pharmaceutically acceptable salts). Examples of suitable pharmaceutically acceptable salts include inorganic acid addition salts such as sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with an acidic amino acid such as aspartate and glutamate; alkali metal salts such as sodium and potassium; alkaline earth metal salts such as magnesium and calcium; ammonium salt; organic basic salts such as trimethylamine, triethylamine, pyridine, picoline, dicyclohexylamine, and N5N'-dibenzylethylenediamine; and salts with a basic amino acid such as lysine and arginine. The salts can be in some cases hydrates or ethanol solvates. The stoichiometry of the salt will vary with the nature of the components. Representative compounds include

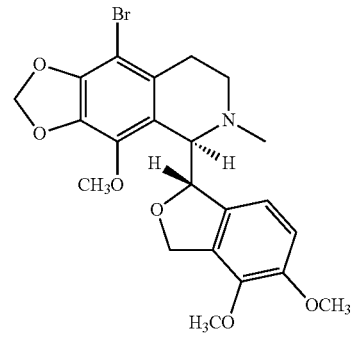

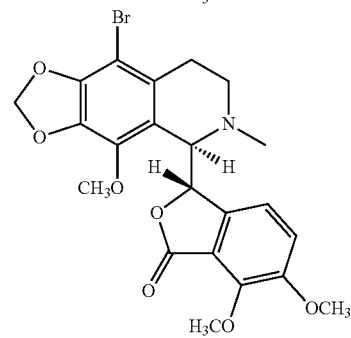

The compounds described herein may be administered in the form of prodrugs. By "prodrug" is meant, for example, any compound (whether itself active or inactive) that is converted chemically in vivo into a biologically active compound as described herein following administration of the prodrug to a subject.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds according to formula A.

The compounds can be prepared by performing electrophilic aromatic substitution on the isoquinoline ring of noscapine, typically under conditions that do not result in significant hydrolysis of the noscapine framework. The substituents typically are added to the 9-position on the isoquinoline ring, although yields can be optimized and by-products may be present and need to be removed during a purification step. More optimized syntheses of representative compounds, such as 9-bromo-nos and Red-9-bromo-nos, are provided in the examples section.

Briefly, the nitration of the isoquinoline ring in noscapine can be accomplished by using stoichiometric silver nitrate and a slight excess of trifluoroacetic anhydride.

The halogenation of noscapine involved various procedures, which varied depending on the particular halogen, as summarized below in Scheme 1.

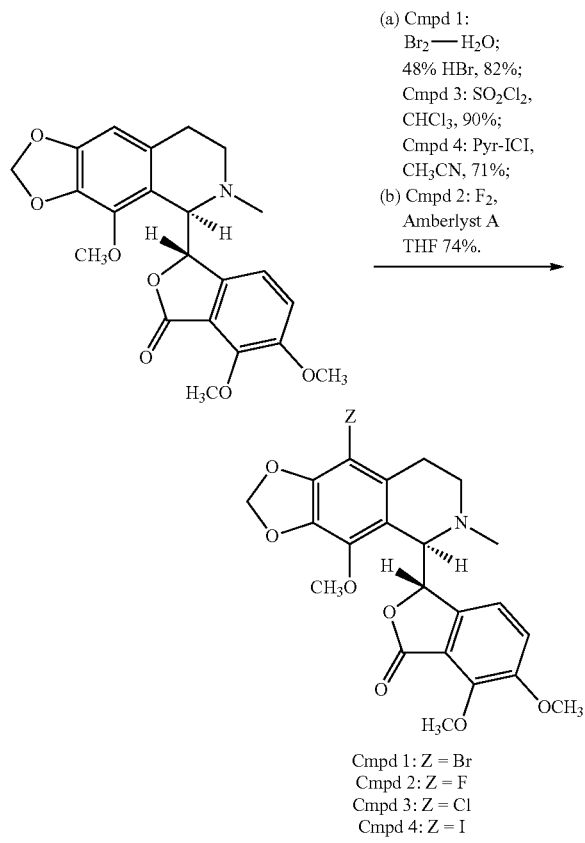

Scheme 1

(a) Cmpd 1:
Br$_2$ — H$_2$O;
48% HBr, 82%;
Cmpd 3: SO$_2$Cl$_2$,
CHCl$_3$, 90%;
Cmpd 4: Pyr-ICl,
CH$_3$CN, 71%;
(b) Cmpd 2: F$_2$,
Amberlyst A
THF 74%.

Cmpd 1: Z = Br
Cmpd 2: Z = F
Cmpd 3: Z = Cl
Cmpd 4: Z = I

Noscapine can be brominated at the 9-position by reacting noscapine with concentrated hydrobromic acid. Noscapine can be fluorinated using the fluoride form of Amberlyst-A 26, or by Br/F exchange. Iodination of noscapine typically required low-acid conditions. One successful approach for preparing 9-Iodo-nos involved treating a solution of noscapine in acetonitrile with pyridine-iodine chloride at room temperature for 6 hours followed by raising the temperature to 100° C. for another 6 hours.

Conjugates of noscapine and folic acid analogs are provided in WO 2010/083104 hereby incorporated by reference.

For those skilled in the art, incorporation of other substituents onto the 9-position of the isoquinoline ring, and other positions in the noscapine framework, can be readily realized. Such substituents can provide useful properties in and of themselves or serve as a handle for further synthetic elaboration.

I. Therapeutic Uses

The present invention provides noscapine analogs of formula A or their pharmaceutically acceptable salts, esters, salts of esters, prodrugs, or salts of prodrugs, for the treatment of a host with diseases caused by innate immune disorder. Alternatively, the noscapine analogs of formula A or its pharmaceutically acceptable salt, ester, salt of ester, prodrug, or salt of prodrug, can be used for the treatment of inflammatory diseases. Specifically, the invention also includes compounds, compositions, and methods for treating or preventing the following:

(a) inflammatory diseases, including Alzheimer's disease, arthritis, asthma, atherosclerosis, Crohn's disease, colitis, dermatitis, diverticulitis, hepatitis, irritable bowel syndrome (IBS), inflammatory bowel disease (IBD), lupus erythematous, nephritis, Parkinson's disease;

(b) abnormal cellular proliferation, including psoriasis, eczema, atherosclerosis, asthma, arthritis, osteoporosis, leukemia, and malignant tumors.

Treatments with one or more of these compounds significantly inhibit TNFα, IL-8 and nitric oxide release upon challenge with various TLR and non-TLR ligands mimicking septic and sterile innate immune pathways. The pharmaceutical compositions include an effective amount of the compounds described herein, along with a pharmaceutically acceptable carrier or excipient. When employed in effective amounts, the compounds can act as a therapeutic agent to prevent and/or treat a wide variety of inflammatory diseases, and are believed to be both safe and effective in this role. Representative inflammatory diseases that can be treated and/or prevented include Alzheimer's disease, arthritis, asthma, atherosclerosis, Crohn's disease, colitis, dermatitis, diverticulitis, hepatitis, irritable bowel syndrome (IBS), inflammatory bowel disease (IBD), lupus erythematous, nephritis and Parkinson's disease.

Within an aspect of the invention is provided a method for treating inflammation, comprising administering a therapeutically sufficient amount of a brominated noscapine analogue to a mammal, wherein administration of the analogue results in a clinically significant improvement in the inflammatory condition of the mammal. Within one embodiment, the clinically significant improvement in the inflammatory condition is selected from the group consisting of: a) a decrease or inhibition in pain; b) a decrease or inhibition in swelling; c) a decrease or inhibition in redness; d) a decrease or inhibition in heat; e) and a decrease or inhibition in loss of function.

Within another aspect, the invention provides a method for treating inflammation, comprising administering a therapeutically sufficient amount of a noscapine analogue to a mammal, wherein the inflammatory condition of the mammal is associated with an autoimmune disease. Within an embodiment, the inflammation is associated with a rheumatic disorder. Within a further embodiment, the rheumatic disorder is rheumatoid arthritis, system lupus erythematosus, a vasculitic disorder, or another rheumatic disorder.

Within another aspect, the invention provides a method for treating inflammation, comprising administering a therapeutically sufficient amount of a noscapine analogue to a mammal, wherein the inflammation is associated with an allergic response.

Within another aspect, the invention provides a method for treating inflammation, comprising administering a therapeutically sufficient amount of a noscapine analogue to a mammal, wherein the inflammation is located in the respiratory tract. Within an embodiment, the inflammation is located in the lung, or sinus. Within another embodiment, the inflammation is associated with asthma, chronic obstructive pulmonary disease, chronic bronchitis, or emphysema.

Within another aspect, the invention provides a method for treating inflammation, comprising administering a therapeutically sufficient amount of a noscapine analogue to a mammal, wherein the inflammation is located on the epidermis. Within an embodiment, the inflammation is associated with psoriasis, or dermatitis.

Within another aspect, the invention provides a method for treating inflammation, comprising administering a therapeutically sufficient amount of a noscapine analogue to a mammal, wherein the inflammation is located in the gastrointestinal tract. Within an embodiment, the inflammation is associated with Inflammatory Bowel disease, ulcerative colitis, Crohn's disease, or inflammation associated diarrhea.

Within another aspect, the invention provides a method for treating inflammation, comprising administering a therapeutically sufficient amount of a noscapine analogue to a mammal, wherein the inflammation is associated with Graft versus Host Disease. Within an embodiment, the inflammation is associated with single-organ or multi-organ failure.

Within another aspect, the invention provides a method for treating inflammation, comprising administering a therapeutically sufficient amount of a noscapine analogue to a mammal, wherein the inflammation is associated with sepsis.

Within another aspect, the invention provides a method for treating inflammation, comprising administering a therapeutically sufficient amount of a noscapine analogue to a mammal, wherein the inflammation is located in the liver. Within an embodiment, the inflammation is associated with chronic active hepatitis, alcoholic liver disease, or non-alcoholic fatty liver disease.

Within another aspect, the invention provides a method for treating inflammation, comprising administering a therapeutically sufficient amount of a noscapine analogue to a mammal, wherein the mammal has a disease selected from the group consisting of: rheumatoid arthritis, systemic lupus erythematosus, polyarteritis nodosa, Wegener's granulomatosis, giant cell arteritis, renal disease, allergic disease, asthma, chronic obstructive pulmonary disease, chronic bronchitis, emphysema, psoriasis, inflammatory bowel disease, ulcerative colitis, Crohn's disease, chronic active hepatitis, alcoholic liver disease, hepatic disease, acute lymphocytic leukemia, lymphomas, sarcoidosis, thrombocytopenia, autoimmune hemolytic anemia, organ transplantation, stroke, spinal cord injury, drug reactions, urticaria, subacute hepatic necrosis, multiple myeloma, idiopathic thrombocytopenic purpura, acquired hemolytic anemia and malignant hyperthermia.

Within another aspect, the invention provides a method for treating inflammation, comprising administering a therapeutically sufficient amount of a noscapine analogue to a mammal, wherein treatment with the noscapine analogue is used as an alternative to glucocorticoid treatment, and wherein administration of the noscapine analogue results in a clinically significant improvement in the inflammatory condition of the mammal.

Within another aspect, the invention provides a method for treating inflammation, comprising administering a therapeutically sufficient amount of a noscapine analogue to a mammal, wherein treatment with the noscapine analogue is used as an alternative to glucocorticoid treatment, and wherein administration of the polypeptide prevents or reduces a glucocorticoid-induced adverse side-effect. Within an embodiment, the glucocorticoid-induced adverse side-effect is selected from the group consisting of: adrenocortical suppression, osteoporosis, bone necrosis, steroid-induced cataracts, steroid-induced obesity, corticosteroid-induced psychosis, gastrointestinal hemorrhage, thymic atrophy, and benign intracranial hypertension.

Within another aspect, the invention provides a method for reducing inflammation, comprising administering a therapeutically sufficient amount of a noscapine analogue to a mammal, wherein administration of the polypeptide results in a clinically significant improvement in the inflammatory condition of the mammal. Within an embodiment, the clinically significant improvement in the inflammatory condition is selected from the group consisting of: a) a decrease or inhibition in pain; b) a decrease or inhibition in swelling; c) a decrease or inhibition in redness; a d) decrease or inhibition in heat; and e) a decrease or inhibition in loss of function.

Within another aspect, the invention provides a method for reducing inflammation, comprising administering a therapeutically sufficient amount of a noscapine analogue to a mammal, wherein the inflammation is acute or chronic. Within an embodiment, the inflammation or inflammatory condition is associated with an autoimmune disease.

Within another aspect, the invention provides a method for reducing inflammation, comprising administering a therapeutically sufficient amount of a noscapine analogue to a mammal, wherein the inflammation is located in the respiratory tract, on the epidermis, in the gastrointestinal tract, or the liver. Within an embodiment, the mammal has a disease selected from the group consisting of: rheumatoid arthritis, systemic lupus erythematosus, polyarteritis nodosa, Wegener's granulomatosis, giant cell arteritis, renal disease, allergic disease, asthma, chronic obstructive pulmonary disease, chronic bronchitis, emphysema, psoriasis, inflammatory bowel disease, ulcerative colitis, Crohn's disease, chronic active hepatitis, alcoholic liver disease, hepatic disease, non-alcoholic fatty liver disease, acute lymphocytic leukemia, lymphomas, sarcoidosis, thrombocytopenia, autoimmune hemolytic anemia, organ transplantation, stroke, spinal cord injury, drug reactions, urticaria, subacute hepatic necrosis, multiple myeloma, idiopathic thrombocytopenic purpura, acquired hemolytic anemia and malignant hyperthermia.

Within another aspect, the invention provides a method for reducing inflammation, comprising administering a therapeutically sufficient amount of a noscapine analogue to a mammal, wherein the noscapine analogue is used as an alternative to glucocorticoid treatment.

Within another aspect, the invention provides a method for reducing inflammation, comprising administering a therapeutically sufficient amount of a noscapine analogue to a mammal, wherein treatment with the noscapine analogue prevents or reduces a glucocorticoid-induced adverse side-effect. Within an embodiment, the glucocorticoid-induced adverse side-effect is selected from the group consisting of: adrenocortical suppression, osteoporosis, bone necrosis, steroid-induced cataracts, steroid-induced obesity, corticosteroid-induced psychosis, gastrointestinal hemorrhage, thymic atrophy, and benign intracranial hypertension.

Within another aspect, the invention provides a method for treating inflammation, comprising administering a therapeutically sufficient amount of a noscapine analogue to a mammal in conjunction with one or more glucocorticoids, wherein administration of the polypeptide results in a clinically significant improvement in the inflammatory condition of the mammal. Within another embodiment, the clinically significant improvement in the inflammatory condition is selected from the group consisting of: a) a decrease or inhibition in pain; b) a decrease or inhibition in swelling; c) a decrease or inhibition in redness; d) a decrease or inhibition in heat; and e) a decrease or inhibition in loss of function.

Within another aspect, the invention provides a method for treating inflammation, comprising administering a therapeutically sufficient amount of a noscapine analogue to a mammal in conjunction with one or more glucocorticoids, wherein the inflammation is acute.

Within another aspect, the invention provides a method for treating inflammation, comprising administering a therapeutically sufficient amount of a noscapine analogue to a mammal in conjunction with one or more glucocorticoids, wherein the inflammation is chronic.

Within another aspect, the invention provides a method for treating inflammation, comprising administering a therapeutically sufficient amount of a noscapine analogue to a mammal in conjunction with one or more glucocorticoids, wherein administration of the agent results in a clinically significant improvement in the inflammatory condition of the mammal, wherein the inflammation or inflammatory condition is associated with an autoimmune disease. Within an embodiment, the inflammation is associated with a rheumatic disorder. Within further embodiment, the rheumatic disorder is rheumatoid arthritis, system lupus erythematosus, a vasculitic disorder, or another rheumatic disorder.

Within another aspect, the invention provides a method for treating inflammation, comprising administering a therapeutically sufficient amount of a noscapine analogue to a mammal in conjunction with one or more glucocorticoids, wherein the inflammation is associated with an allergic response. Within an embodiment, the inflammation is located in the respiratory tract. Within a further embodiment, the inflammation is associated with asthma, chronic obstructive pulmonary disease, chronic bronchitis, or emphysema.

Within another aspect, the invention provides a method for treating inflammation, comprising administering a therapeutically sufficient amount of a noscapine analogue to a mammal in conjunction with one or more glucocorticoids, wherein administration of the polypeptide results in a clinically significant improvement in the inflammatory condition of the mammal, wherein the inflammation is located on the epidermis. Within a further embodiment, the inflammation is associated with psoriasis, or dermatitis.

Within another aspect, the invention provides a method for treating inflammation, comprising administering a therapeutically sufficient amount of a noscapine analogue to a mammal in conjunction with one or more glucocorticoids, wherein administration of the polypeptide results in a clinically significant improvement in the inflammatory condition of the mammal, wherein the inflammation is located in the gastrointestinal tract. Within a further embodiment, the inflammation is associated with Inflammatory Bowel disease, ulcerative colitis, Crohn's disease, or inflammation associated diarrhea.

Within another aspect, the invention provides a method for treating inflammation, comprising administering a therapeutically sufficient amount of a noscapine analogue to a mammal in conjunction with one or more glucocorticoids, wherein administration of the polypeptide results in a clinically significant improvement in the inflammatory condition of the mammal, wherein the inflammation is associated with Graft versus Host Disease. Within an embodiment, the inflammation is associated with single-organ or multi-organ failure.

Within another aspect, the invention provides a method for treating inflammation, comprising administering a therapeutically sufficient amount of a noscapine analogue to a mammal in conjunction with one or more glucocorticoids, wherein administration of the agent results in a clinically significant improvement in the inflammatory condition of the mammal, wherein the inflammation is associated with sepsis.

Within another aspect, the invention provides a method for treating inflammation, comprising administering a therapeutically sufficient amount of a noscapine analogue to a mammal in conjunction with one or more glucocorticoids, wherein administration of the agent results in a clinically significant improvement in the inflammatory condition of the mammal, wherein the inflammation is located in the liver. Within an embodiment, the inflammation is associated with chronic active hepatitis, alcoholic liver disease, or non-alcoholic fatty liver disease.

Within another aspect, the invention provides a method for treating inflammation, comprising administering a therapeutically sufficient amount of a noscapine analogue to a mammal in conjunction with one or more glucocorticoids, wherein administration of the agent results in a clinically significant improvement in the inflammatory condition of the mammal, wherein the mammal has a disease selected from the group consisting of: rheumatoid arthritis, systemic lupus erythematosus, polyarteritis nodosa, Wegener's granulomatosis, giant cell arteritis, renal disease, allergic disease, asthma, chronic obstructive pulmonary disease, chronic bronchitis, emphysema, psoriasis, inflammatory bowel disease, ulcerative colitis, Crohn's disease, chronic active hepatitis, alcoholic liver disease, hepatic disease, acute lymphocytic leukemia, lymphomas, sarcoidosis, thrombocytopenia, autoimmune hemolytic anemia, organ transplantation, stroke, spinal cord injury, drug reactions, urticaria, subacute hepatic necrosis, multiple myeloma, idiopathic thrombocytopenic purpura, acquired hemolytic anemia and malignant hyperthermia.

Within another aspect the invention provides a method for treating an inflammatory condition, comprising administering a therapeutically sufficient amount of a brominated noscapine analogue to a mammal in conjunction with one or more glucocorticoids, wherein treatment with the brominated noscapine analogue prevents or reduces a glucocorticoid-induced adverse side-effect. Within an embodiment, the glucocorticoid-induced adverse side-effect is selected from the group consisting of: adrenocortical suppression, osteoporosis, bone necrosis, steroid-induced cataracts, steroid-induced obesity, corticosteroid-induced psychosis, gastrointestinal hemorrhage, thymic atrophy, and benign intracranial hypertension. Within another embodiment, the level of glucocorticoid is reduced compared to treatment without the brominated noscapine analogue. Within another embodiment, the inflammatory condition is selected from the group consisting of: a) a decrease or inhibition in pain; b) a decrease or inhibition in swelling; c) a decrease or inhibition in redness; d) a decrease or inhibition in heat; and e) a decrease or inhibition in loss of function. Within another embodiment, the noscapine analogue and the glucocorticoid are administered concurrently. Within another embodiment, the noscapine analogue and the glucocorticoid are administered sequentially. Within another embodiment, the glucocorticoid is short-acting, intermediate-acting, or long-acting.

Within another aspect, the invention provides a method for treating inflammation or an inflammatory condition in a mammal, comprising administering a therapeutically sufficient amount of a noscapine analogue to a mammal in conjunction with one or more glucocorticoids, wherein administration of the agent results in a clinically significant improvement in the inflammation or inflammatory condition of the mammal, and wherein the glucocorticoid is selected from the group consisting of alclometasone dipropionate, amcinonide, beclomethasone dipropionate, betamethasone, betamethasone benzoate, betamethasone dipropionate, betamethasone sodium, betamethasone valerate, clobetasol propionate, clocortolone pivalate, hydrocortisone, hydrocortisone acetate, hydrocortisone butyrate, hydrocortisone cypionate, hydrocortisone sodium phosphate, hydrocortisone sodium succinate, hydrocortisone valerate, cortisone acetate, desonide, desoximetasone, dexamethasone, dexamethasone acetate, dexamethasone sodium, diflorasone diacetate, fludrocortisone acetate, flunisolide, fluocinolone acetonide, fluocinonide, fluorometholone, flurandrenolide, halcinonide, medrysone, methylprednisolone, methylprednisolone acetate, methylprednisolone sodium, mometasone furoate, paramethasone acetate, prednislone, prednislone acetate, prednislone sodium phosphate, prednisolone tebutate, prednisone, triamcinolone, triamcinolone acetonide, triamcinolone diacetate and triamcinolone hexacetonide. Within an embodiment, the glucocorticoid is administered as a derivative of alclometasone dipropionate, amcinonide, beclomethasone dipropionate, betamethasone, betamethasone benzoate, betamethasone dipropionate, betamethasone sodium, betamethasone valerate, clobetasol propionate, clocortolone pivalate, hydrocortisone, hydrocortisone acetate, hydrocortisone butyrate, hydrocortisone cypionate, hydrocortisone sodium phosphate, hydrocortisone sodium succinate, hydrocortisone valerate, cortisone acetate, desonide, desoximetasone, dexamethasone, dexamethasone acetate, dexamethasone sodium, diflorasone diacetate, fludrocortisone acetate, flunisolide, fluocinolone acetonide, fluocinonide, fluorometholone, flurandrenolide, halcinonide, medrysone, methylprednisolone, methylprednisolone acetate, methylprednisolone sodium, mometasone furoate, paramethasone acetate, prednislone, prednislone acetate, prednislone sodium phosphate, prednisolone tebutate, prednisone, triamcinolone, triamcinolone acetonide, triamcinolone diacetate or triamcinolone hexacetonide.

Within another aspect, the invention provides a method for treating inflammation or an inflammatory condition in a mammal, comprising administering a therapeutically sufficient amount of a noscapine analogue to a mammal in conjunction with one or more glucocorticoids, wherein administration of the polypeptide results in a decrease of a proinflammatory indicator. Within an embodiment, the proinflammatory indicator is measured by serum levels of pro-inflammatory cytokines or inflammation associated neutrophil infiltration.

II. Pharmaceutical Compositions

The compounds described herein can be incorporated into pharmaceutical compositions and used to prevent a condition or disorder in a subject susceptible to such a condition or disorder, and/or to treat a subject suffering from the condition or disorder. The pharmaceutical compositions described herein include one or more of the noscapine analogues described herein, and/or pharmaceutically acceptable salts thereof. Optically active compounds can be employed as racemic mixtures, as pure enantiomers, or as compounds of varying enantiomeric purity.

The manner in which the compounds are administered can vary. The compositions are preferably administered orally (e.g., in liquid form within a solvent such as an aqueous or non-aqueous liquid, or within a solid carrier). Preferred compositions for oral administration include pills, tablets, capsules, caplets, syrups, and solutions, including hard gelatin capsules and time-release capsules. Compositions may be formulated in unit dose form, or in multiple or subunit doses. Preferred compositions are in liquid or semisolid form. Compositions including a liquid pharmaceutically inert carrier such as water or other pharmaceutically compatible liquids or semisolids may be used. The use of such liquids and semisolids is well known to those of skill in the art.

The compositions can also be administered via injection, i.e., intraveneously, intramuscularly, subcutaneously, intraperitoneally, intraarterially, intrathecally; and intracerebroventricularly. Intravenous administration is a preferred method of injection. Suitable carriers for injection are well known to those of skill in the art, and include 5% dextrose solutions, saline, and phosphate buffered saline. The compounds can also be administered as an infusion or injection (e.g., as a suspension or as an emulsion in a pharmaceutically acceptable liquid or mixture of liquids).

The formulations may also be administered using other means, for example, rectal administration. Formulations useful for rectal administration, such as suppositories, are well known to those of skill in the art. The compounds can also be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); or transdermally (e.g., using a transdermal patch, using technology that is commercially available from Novartis and Alza Corporation). Although it is possible to administer the compounds in the form of a bulk active chemical, it is preferred to present each compound in the form of a pharmaceutical composition or formulation for efficient and effective administration.

Exemplary methods for administering such compounds will be apparent to the skilled artisan. The usefulness of these formulations may depend on the particular composition used and the particular subject receiving the treatment. These formulations may contain a liquid carrier that may be oily, aqueous, emulsified or contain certain solvents suitable to the mode of administration.

The compositions can be administered intermittently or at a gradual, continuous, constant or controlled rate to a warm-blooded animal (e.g., a mammal such as a mouse, rat, cat, rabbit, dog, pig, cow, or monkey), but advantageously are administered to a human being. In addition, the time of day and the number of times per day that the pharmaceutical formulation is administered can vary.

Preferably, the compositions are administered such that active ingredients interact with regions where inflammatory cells are located. The compounds described herein are very potent at treating these inflammations.

In certain circumstances, the compounds described herein can be employed as part of a pharmaceutical composition with other compounds intended to prevent or treat a particular inflammatory disease, i.e., combination therapy. In addition to effective amounts of the compounds described herein, the pharmaceutical compositions can also include various other components as additives or adjuncts.

III. Combination Therapy

The combination therapy may be administered as (a) a single pharmaceutical composition which comprises a noscapine analogue as described herein, at least one additional pharmaceutical agent described herein, and a pharmaceutically acceptable excipient, diluent, or carrier; or (b) two separate pharmaceutical compositions comprising (i) a first composition comprising a noscapine analogue as described herein and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions can be administered simultaneously or sequentially and in any order.

In use in treating or preventing inflammatory diseases, the noscapine analogues described herein can be administered together with at least one other anti-inflammatory agent as part of a unitary pharmaceutical composition. Alternatively, the noscapine analogues can be administered apart from the other anti-inflammatory agent. In this embodiment, the noscapine analogues and the at least one other anti-inflammatory agent are administered substantially simultaneously, i.e. the compounds are administered at the same time or one after the other, so long as the compounds reach therapeutic levels for a period of time in the blood.

Combination therapy involves administering a noscapine analogue, as described herein, or a pharmaceutically acceptable salt or prodrug of a compound described herein, in combination with at least one anti-inflammatory agent, ideally one which functions by a different mechanism.

Examples of known anti-inflammatory agents which can be used for combination therapy include, but are not limited to, non-steroidal anti-inflammatory drugs, steroids, anticoagulants, antithrombotic drugs, antibacterial agents, antifungal agents, antivirus drugs, thrombolytic drugs, methemoglobin increase preventive drugs, immunomodulators, antiprotozoals, antitussive and expectorant drugs, sedatives, anesthetics, antinarcotics, antiulcer drugs, hyperlipidemia treating agents, therapeutic agents for arteriosclerosis, HDL increasing agents, unstable plaque stabilizing agents, myocardial protecting agent, hypothyroidism treating agent, nephrotic syndrome treating agent, chronic renal failure treating agent, diuretics, hypertension treating agents, cardiac failure treating agents, muscle relaxants, anticonvulsants, cardiacs, vasodilators, vasoconstrictors, antiarrhythmics, antidiabetic drugs, agents for improving prognosis after coronary bypass surgery, hypertensors, tranquilizers, antipsychotics, antiemetics, therapeutic agents for Alzheimer's diseases, anti-Parkinson drugs, therapeutic agents for amyotrophic spinal lateral sclerosis, neurotrophic factors, antidepressants, therapeutic agents for schizophrenia, antitumor drugs, vitamins, vitamin derivatives, therapeutic agents for arthritis, antirheumatics, antiallergic drugs, antiasthmatics, therapeutic agents for atopic dermatitis, therapeutic agents for allergic rhinitis, therapeutic agents for pollakisuria/anischuria, protease drugs, protease inhibitors, anti-SIDS drugs, anti-sepsis drugs, anti-septic shock drugs, endotoxin-antagonists or -antibodies, signal transduction inhibitors, inhibitors of inflammatory mediator activity, antibodies to inhibit inflammatory mediator activity, inhibitors of inflammatory mediator production, inhibitors of anti-inflammatory mediator activity, antibodies to inhibit anti-inflammatory mediator activity, inhibitors of anti-inflammatory mediator production, al-adrenergic agonists, cytopathy suppressive drug and the like. Of these, antibacterial agents, antifungal agents, antivirus agents, non-steroidal anti-inflammatory drugs, steroids, anticoagulants, cytopathy suppressive drugs, anti-sepsis drugs and the like are preferable. Specifically, the following agents can be mentioned: colchicines, taxanes (such as taxol, taxotere), vincas (such as vinblastine, vincristine).

Any of the above-mentioned compounds can be used in combination therapy with the noscapine analogues. Preferably, the effective amount is sufficient to obtain the desired result, but insufficient to cause appreciable side effects.

In another embodiment, for the treatment of, the active compound or its derivative or salt can be administered in combination or alternation with another anti-inflammatory agent, such as a agent, including those of the formula above. In general, in combination therapy, an effective dosage of two or more agents are administered together, whereas during alternation therapy, an effective dosage of each agent is administered serially. The dosages will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

EXPERIMENTAL

Noscapine analogs were synthesized according to previously reported methods. [Zhou et al. (2003) Mol Pharmacol 63: 799-807 and Aneja et al. (2006) Biochem Pharmacol 72:415-426]. RPMI 1640 medium, Dulbecco's Eagle medium, fetal bovine serum (FBS), penicillin/streptomycin, sodium pyruvate and nonessential amino acids were obtained from Cellgro (Mediatech Herndon, Va.). Autophagy inhibitor 3-methyladenine (3-MA) was purchased from Sigma (St Louis, Mo.). Synthetic TLR2 ligand Pam3CSK4, embryonic kidney 293 HEK-TLR2/6, HEK-TLR2 and HEKTLR4-MD2-CD14 stably transfected cells were purchased from InvivoGen (San Diego, Calif.). Macrophage cell lines THP-1, RAW264.7 and 23ScCr were purchased from ATCC.

One prepares (S)-6,7-Dimethoxy-3-((R)-4-methoxy-6-methyl-9-nitro-5,6,7,8-tetrahydro-[1,3]dioxolo[4,5-g]isoquinolin-5-yl)isobenzofuran-1(3H)-one (9-nitro-nos) by the aromatic nitration of (S)-6,7-dimethoxy-3-((R)-4-methoxy-6-methyl-5,6,7,8-tetrahydro-[1,3]dioxolo[4,5-g]isoquinolin-5-yl)isobenzo-furan-1(3H)-one (noscapine) using silver nitrate in acetonitrile and TFAA at 25° C. in accordance with the procedures disclosed in WO2008/109609.

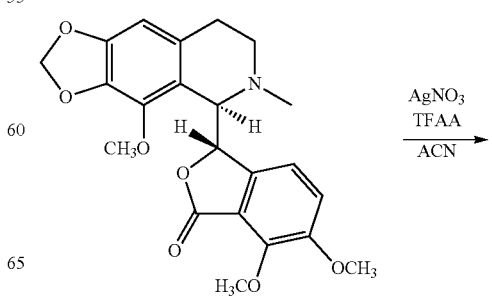

-continued

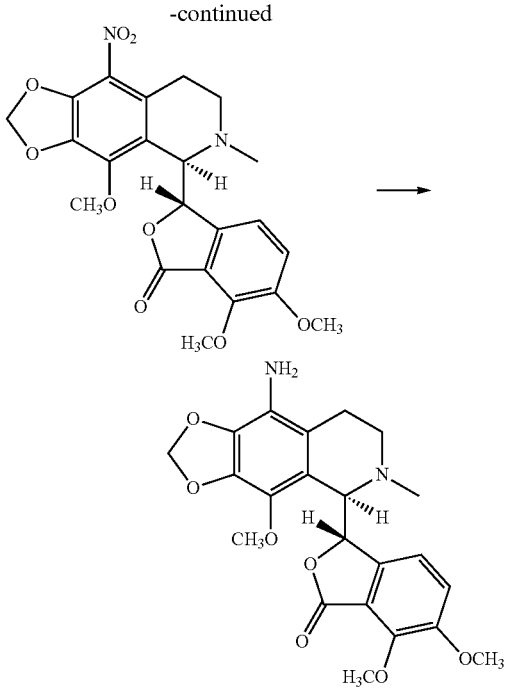

Reduction of the nitro group to an amine allows for amino acid couplings or transformation to other derivative such as alkyl amides, secondary and tertiary amines, etc.

Cell Cultures

THP-1 human macrophage-like cells were grown in RPMI 1640 with L-glutamate supplemented with 10% FBS, 50 IU/ml of penicillin, 50 μg/ml of streptomycin, 1% sodium pyruvate and 1% non-essential amino acids. Culture flasks were incubated at 37° C. with humidity under 5% $CO_2$. Murine macrophages (RAW 264.7, 23ScCr) and human kidney epithelial cells HEK293 were grown in Dulbecco's Eagle medium supplemented and incubated as mentioned above.

LPS Purification and Quantitation

Lipopolysaccharide (LPS) or endotoxin is a well-characterized TLR4-MD-2 ligand. Endotoxin from the serogroup B Niesseria meningitidis strain NMB was initially extracted from whole meningococci by the phenol-water method. The endotoxin preparations were further purified and quantified as described [Zughaier S M, Tzeng Y L, Zimmer S M, Datta A, Carlson R W, et al. (2004) Neisseria meningitidis lipooligosaccharide structure-dependent activation of the macrophage CD14/Toll-like receptor 4 pathway. Infect Immun 72: 371-380.]. Briefly, residual membrane phospholipids were removed by repeated extraction of the dried LPS (also known as lipooligosaccharide or LOS) samples with 9:1 ethanol: water. The expected fatty acyl components of 3-OHC12:0, 3-OHC14:0 and C12:0 and the absence of membrane phospholipids was assessed by mass spectroscopy (GC-MS) (Dr Russell Carlson, Complex Carbohydrate Research Center, University of Georgia, Athens, Ga.). Endotoxin stock solutions were prepared in pyrogen free water at 10 nmole/ml concentration and further diluted with endotoxin free PBS to 1 nmole/ml and 100 pmole/ml with extensive vortex and sonication prior to each dilution [Zughaier S M, Tzeng Y L, Zimmer S M, Datta A, Carlson R W, et al. (2004) Neisseria meningitidis lipooligosaccharide structure-dependent activation of the macrophage CD14/Toll-like receptor 4 pathway. Infect Immun 72: 371-380; Zughaier S M, Zimmer S M, Datta A, Carlson R W, Stephens D S (2005) Differential induction of the toll-like receptor 4-MyD88-dependent and -independent signaling pathways by endotoxins. Infect Immun 73: 2940-2950.].

Cellular Activation and Inflammatory Responses

The effect of noscapine analogs was investigated in time-course and dose-response experiments in well established human and murine cell lines. Human THP-1 (a macrophage-like cell line), murine RAW 264.7 (TLR4-sufficient), 23ScCr (TLR4-deficient), HEK-TLR2/6 and HEK-TLR4-MD2-CD14 stably transfected cell lines were treated with noscapine or its analogs at 10, 25 and 50 μM for either 1, 2, 4 hr or overnight prior to stimulation with TLR ligands mimicking septic inflammation or non-TLR ligands mimicking sterile inflammation. Alternatively, cells were co-treated with noscapine or its analogs (50 μM) and TLR ligands or non-TLR ligand e.g. recombinant cytokines/chemokines were then incubated overnight. TLR ligand concentrations ranging from (LPS: 10-0.31 picomolar (pM) and Pam3CSK4: 10-0.31 μg/ml) and non-TLR ligands (mouse IP-10 and TNFα: 1000-31 pg/ml) were made in duplicate wells using sterile PBS by serial fold dilutions in the 96-well tissue culture plates at 50 μl final volumes. Freshly grown THP-1cells, RAW264.7, ScCr, HEK-TLR2/6 and HEK-TLR4-MD2-CD14 transfected cells each adjusted to $10^6$ cell/ml and 250 μl aliquots were dispensed into each well at a final cell density of $250 \times 10^3$ in the designated 96-well plates. The plates were then incubated overnight at 37° C. with 5% $CO_2$ and humidity. Supernatants from stimulated cells were harvested and stored at −20° C. until further use. In certain experiments THP-1 and RAW264.7 cells were pretreated with 50 μM of 3-MA, the pharmacological inhibitor of autophagy, for 30 min prior to cotreatment with TLR ligand and noscapine analogs.

Cytokine and Chemokine Profiles

Released cytokines TNFα and IL-6 and chemokines CXCL10 (IP-10), MIP-2α and IL-8 were quantified by DuoSet ELISA (R&D Systems, Minneapolis, Minn.) following the manufacturer's instructions as previously described [Zughaier S M, Zimmer S M, Datta A, Carlson R W, Stephens D S (2005) Differential induction of the toll-like receptor 4-MyD88-dependent and -independent signaling pathways by endotoxins. Infect Immun 73: 2940-2950.].

Nitric Oxide Induction by Murine Macrophages

Freshly grown adherent RAW 246.7 or 23ScCr (TLR4-deficient) macrophages were scraped by a cell scraper. Harvested cells were washed and re-suspended in Dulbecco's complete media, counted and adjusted to $10^6$ cell/ml. 250 ml aliquots were then dispensed into each well at final $250 \times 10^3$ cell density in the designated 96-well plates prior to stimulation with TLR ligands or recombinant cytokines as mentioned above. The induced RAW 264.7 or 23ScCr macrophages were incubated overnight at 37° C. with 5% $CO_2$ and supernatants were harvested and saved. Nitric oxide release was quantified using the Griess chemical method as previously described [Zughaier S M, Tzeng Y L, Zimmer S M, Datta A, Carlson R W, et al. (2004) Neisseria meningitidis lipooligosaccharide structure-dependent activation of the macrophage CD14/Toll-like receptor 4 pathway. Infect Immun 72: 371-380.].

Cellular Viability and Proliferation Assessment

The toxicity of noscapine or its analogs was determined by assessing cellular viability and proliferation using trypan blue exclusion method [Prise K M, Gaal J C, Pearson C K (1986) Increased protein ADPribosylation in HeLa cells exposed to the anti-cancer drug methotrexate. Biochim Biophys Acta 887: 13-22.]. Cells were grown at a starting density of 0.75 million cell/ml (final volume 2 ml) in presence of increasing doses (10, 25 and 50 μM/10⁶ cells) of noscapine or its analogs for 3 days. Cellular aliquots (100 μl) were taken daily and cells were diluted 1:1 with the vital dye trypan blue 0.4% solution (Cellgro, Mediatech Inc, Herndon, Va.) in PBS and viable cells were counted. LDH release into the supernatant was also measured to assess the toxicity of the drugs. Light microscopy imaging was used to assess cellular morphology of macrophages incubated with or without noscapine analogs [Zughaier S M, Shafer W M, Stephens D S (2005) Antimicrobial peptides and endotoxin inhibit cytokine and nitric oxide release but amplify respiratory burst response in human and murine macrophages. Cell Microbiol 7: 1251-1262.].

Cellular Respiratory Burst (Oxidative Burst) Activity

The enhanced chemiluminescence method was used as previously described [Zughaier S M, Ryley H C, Jackson S K (1999) A melanin pigment purified from an epidemic strain of *Burkholderia cepacia* attenuates monocyte respiratory burst activity by scavenging superoxide anion. Infect Immun 67: 908-913.]. Briefly, freshly grown THP-1 cells were adjusted to $2\times10^6$/ml, transferred to two large tissue culture flasks labeled as primed or unstimulated. Two pmole/ml LPS were added to prime cells or left unstimulated as control cells. Both flasks were incubated overnight at 37° C. under 5% $CO_2$. Primed and control cells were then aliquoted into designated small tissue culture flasks (25 ml volume) and treated with 50 μM of noscapine or its analogs or DMSO for 2 hr or instantly prior to triggering oxidative burst. Unprimed or control cells were also treated with 50 μM of noscapine or its analogs and incubated in the same way but without endotoxin. The cells were collected in universal tubes, washed twice with culture medium and resuspended in standard buffer (4.58 mM $KH_2PO_4$, 8.03 mM $NaHPO_4$, 0.5 mM $MgCl_2$, 0.45 mM $CaCl_2$, 1% (w/v) glucose, 0.033% (w/v) KCl, 0.76% (w/v) NaCl and 0.1% (w/v) endotoxin-free bovine serum albumin (pH 7.3) at $2\times10^6$/ml. The chemiluminescence probe lucigenin (Sigma) was added to the cell suspension (25 μl/ml of cells from 1.0 mM stock solution) and mixed gently. Aliquots (150 μl) of the cellular mixture were transferred into at least quadruplicate wells of a white 96-well plate (FluoroNunc-PolySorp; Nalge Nunc International, Rochester, N.Y.). The respiratory burst was triggered with 50 μl of PMA (1 μM). Chemiluminescence was measured in relative light units (a measure of the number of photons generated by the reaction at each time point). Chemiluminescence was measured using a luminometer (ML3000, Dynatech Laboratories Inc. Chantilly, Va.) and the plate was read immediately and then at 2 min intervals for the next 90 min [Zughaier S M, Ryley H C, Jackson S K (1999) A melanin pigment purified from an epidemic strain of *Burkholderia cepacia* attenuates monocyte respiratory burst activity by scavenging superoxide anion. Infect Immun 67: 908-913].

Electron Microscopy

Human macrophage cells were fixed for 1 hr with 2% glutaraldehyde in 0.1M sodium cacodylate buffer, rinsed in the same buffer and the post-fixed with 2% osmium tetroxide in the same buffer for 1 hr at room temperature. The samples were then dehydrated with a graded ethanol series through $3\times100$%, $2\times$ in propylene oxide and embedded in Spurr's resin. Sections were stained with 1% uranyl acetate and lead citrate. Electron microscopy imaging was then performed at a magnification of $3597\times$.

Detection of Acidic Vesicular Organelles (AVOs)

THP-1 cells were plated on cover slips and allowed to attach. Following treatments for 24 hr with DMSO alone (control), Red-Br-nos, LPS, Red-Br-nos and LPS, cells were stained with 1 μg/ml acridine orange for 15 min, washed with PBS, and examined under a Zeiss fluorescence microscope using a 40× objective lens [Herman-Antosiewicz A, Johnson D E, Singh S V (2006) Sulforaphane causes autophagy to inhibit release of cytochrome C and apoptosis in human prostate cancer cells. Cancer Res 66: 5828-5835.].

Western Blot Analysis

Proteins from THP-1 cells pellets were resolved by polyacrylamide gel-electrophoresis and transferred onto polyvinylidene difluoride membranes (Millipore). The membranes were blocked in Tris-buffered saline containing 0.2% Tween-20 and 5% fat-free dry milk and incubated first with primary antibodies (LC3 and bactin, Cell Signaling) and then with horseradish peroxidase conjugated secondary antibodies (Santa-Cruz). Specific proteins were visualized with enhanced chemiluminescence detection reagent according to the manufacturer's instructions (Pierce Biotechnology).

Statistical Analysis

Mean values of at least 4 independent determinations±SD and p values (Student t test) were calculated in reference to no drug treatment values using the Excel software.

Tubulin Binding Assay:

Fluorescence titration for determining the tubulin binding parameters was performed as described previously (Gupta and Panda, 2002). In brief, 9-bromo-nos (0-100 μM) was incubated with 2 μM tubulin in 25 mM PIPES, pH 6.8, 3 mM MgSO4 and 1 mM EGTA for 45 min at 37° C. The relative intrinsic fluorescence intensity of tubulin was then monitored in a JASCO FP-6500 spectrofluorometer (JASCO, Tokyo, Japan) using a cuvette of 0.3-cm path length, and the excitation wavelength was 295 nm. The fluorescence emission intensity of 9-nitro-nos at this excitation wavelength was negligible. A 0.3-cm path-length cuvette was used to minimize the inner filter effects caused by the absorbance of 9-nitro-nos at higher concentration ranges. In addition, the inner filter effects were corrected using a formula Fcorrected=Fob served*antilog [(Aex+Aem)/2], where Aex is the absorbance at the excitation wavelength and Aem is the absorbance at the emission wavelength. The dissociation constant (Kd) was determined by the formula: 1/B=Kd/[free ligand]+1, where B is the fractional occupancy and [free ligand] is the concentration of free noscapine or 9-nitro-nos. The fractional occupancy (B) was determined by the formula B=ΔF/ΔFmax, where ΔF is the change in fluorescence intensity when tubulin and its ligand are in equilibrium and ΔFmax is the value of maximum fluorescence change when tubulin is completely bound with its ligand. ΔFmax was calculated by plotting 1/ΔF versus 1/ligand using total ligand concentration as the first estimate of free ligand concentration.

Tubulin Polymerization Assay:

Mammalian brain tubulin (1.0 mg/ml) was mixed with different concentrations of 9-bromo-nos (25 or 100 μM) at 0° C. in an assembly buffer (100 mM PIPES at pH 6.8, 3 mM MgSO4, 1 mM EGTA, 1 mM GTP, and 1M sodium glutamate). Polymerization was initiated by raising the temperature to 37° C. in a water bath. The rate and extent of the polymerization reaction were monitored by light scattering at 550 nm, using a 0.3-cm path length cuvette in a JASCO FP-6500 spectrofluorometer (JASCO, Tokyo, Japan) for 30 minutes.

MTS Assay:

Suspension cells (CEM, CEMNLB100 and CEM/VM-1-5) were cultured in RPMI-1640 media containing 10% FBS and then seeded into 96-well plates at a density of $5\times10^3$ cells per well and were treated with increasing gradient concentrations of 9-nitro-nos for 72 hours. Measurement of cell proliferation was performed colorimetrically by 3-(4,5-dimethylthiazol-2-yl)-5-(3-carboxymethoxyphenyl)-2-(4-sulphophenyl)-2H-tetrazolium, inner salt (MTS) assay, using the CellTiter96 AQueous One Solution Reagent (Promega, Madison, Wis.). Cells were exposed to MTS for 3 hours and absorbance was measured using a microplate reader (Molecular Devices, Sunnyvale, Calif.) at an optical density (OD) of 490 nm.

The percentage of cell survival as a function of drug concentration for both the assays was then plotted to determine the IC50 value, which stands for the drug concentration needed to prevent cell proliferation by 50%.

Noscapine Analogs Possess Innate Anti-Inflammatory Activity

Figure 2:
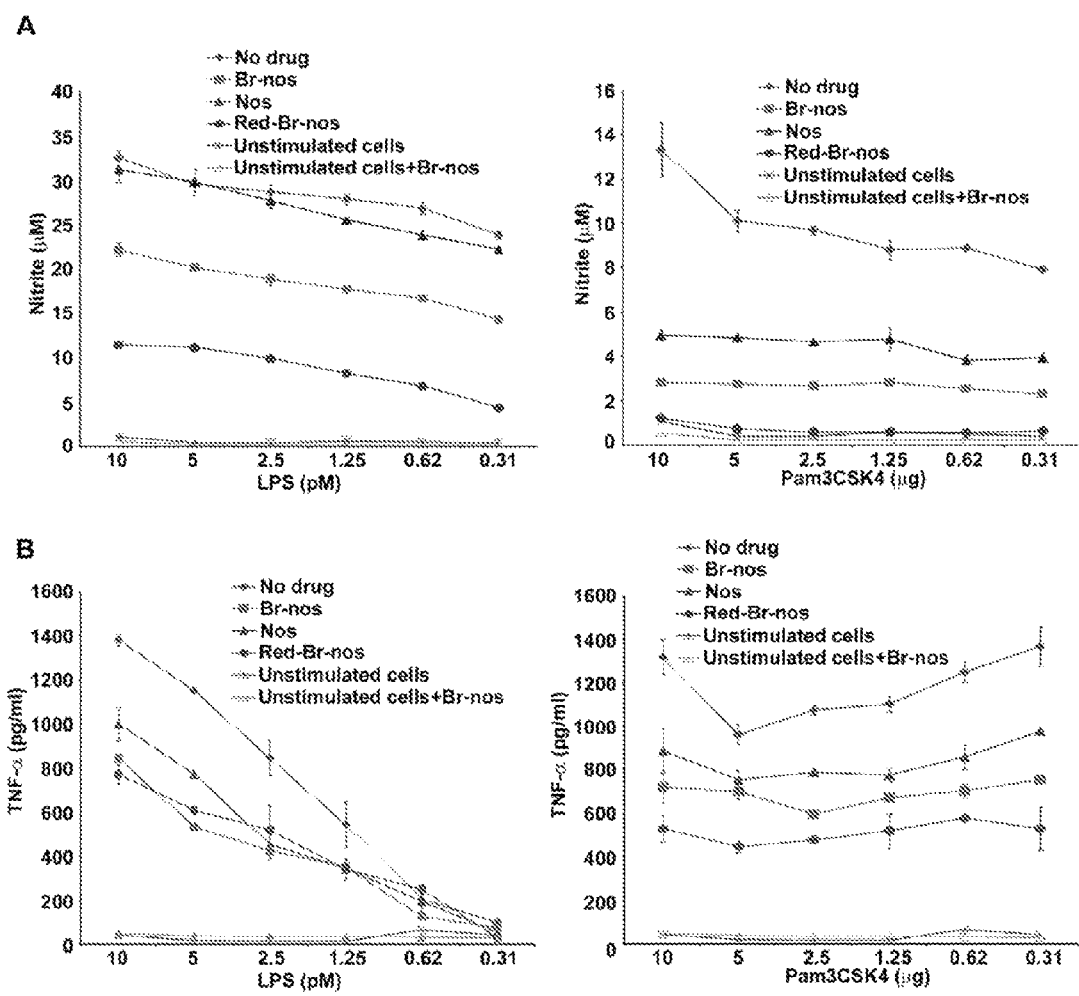
FIG. 2 illustrates co-treatment of murine and human macrophages with noscapine analogs inhibit TLR-induced inflammatory responses. Panel A shows NO release from RAW 264.7 cells co-treated with 50 μM of noscapine and its analogs and varying doses of TLR ligands (LPS, TLR4 ligand or TLR2 ligand Pam3CSK4) overnight. Nitrite accumulation was detected by the Griess method. Panel B shows TNFα release from THP-1 human macrophage like cells co-treated with 50 μM of noscapine and its analogs and TLR ligands as above and incubated overnight. TNFα release was measured in the supernatants by ELISA. No drug refers to RAW264.7 cells treated with DMSO (50 μM) alone followed by LPS or Pam3CSK4 induction. For Nos (noscapine) and the TLR ligands, nitric oxide p value for LPS was=0.03, Pam3CSK4=0.0004 and TNFα p value for LPS=0.0002, Pam3CSK4=0.0004. For Br-nos (9-bromonoscapine) and the TLR ligands p values were <0.0001. For Red-Br-nos (Reduced bromonoscapine) and the TLR ligands p values were <0.00001. Unstimulated cells were used as control and these cells were treated either with DMSO only or Br-nos (50 μM) without the TLR ligand. Error bars represent SD from mean of at least duplicate readings. Data are representative of at least 3 independent experiments. p values were calculated with reference to no drug values.
Figure 3:
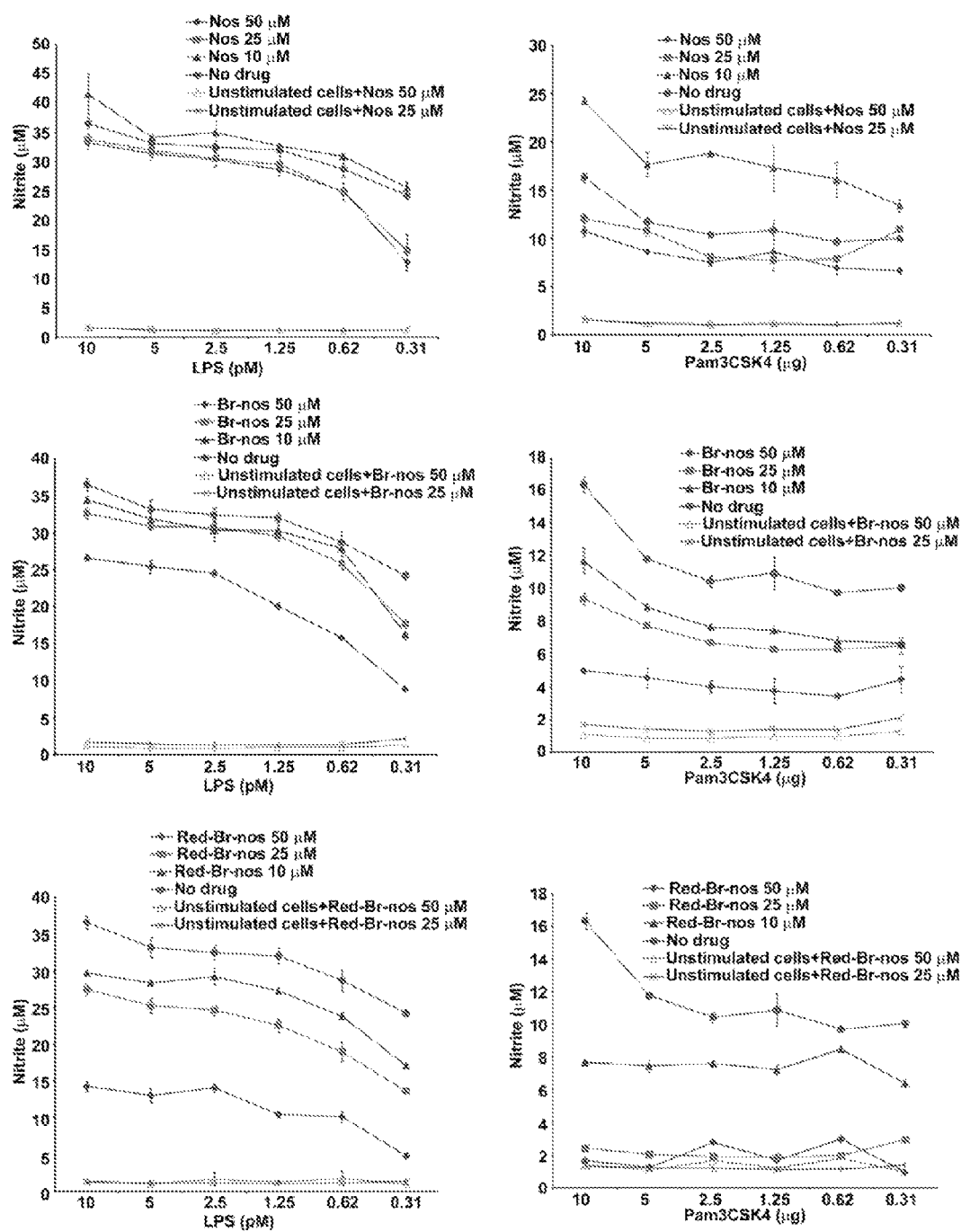
FIG. 3 illustrates dose-dependent anti-inflammatory effects of the noscapine analogs. Nitric oxide release was measured in RAW 264.7 murine macrophages treated with 10, 25 and 50 μM of noscapine analogs for 4 hrs, then stimulated with the TLR4 ligand LPS or the TLR2 ligand Pam3CSK4 and incubated overnight. Nitrite accumulation was detected by the Griess method. Nos refers to noscapine parent analog (10 μM Nos concentration, p value for LPS=0.014, Pam3CSK4=0.0007; 25 μM Nos p value for LPS=0.0001, Pam3CSK4=0.00001; 50 μM Nos p values<0.00001). Br-nos refers to brominated noscapine analog and TLR ligand (10 μM Br-nos p value for LPS=0.001, Pam3CSK4 p<0.00001; 25 μM Br-nos p value for LPS=0.0003, Pam3CSK4, p value<0.00001; 50 μM Br-nos p value<0.00001). Red-Br-nos refers to reduced brominated noscapine and TLR ligand (10, 25 and 50 μM Red-Br-nos p value<0.00001). Unstimulated cells were used as control and were treated with 25 and 50 μM of noscapine analogs. Error bars represent the SD from the mean of at least duplicate readings. These data is representative of 3 independent experiments, and p values were calculated with reference to no drug values.

Noscapine and noscapine analogs (Br-nos and Red-Br-nos) were first investigated in a TLR ligand induced septic inflammation model. Human (THP-1) and murine (RAW 264.7) macrophages were used that usually respond well to a diverse repertoire of pathogens and inflammatory mediators. Macrophages were treated with noscapine or noscapine analogs at 10, 25 and 50 µM prior to stimulation or co-stimulation with highly purified TLR-ligands (meningococcal LPS, a TLR4-MD-2 ligand and the synthetic lipopetide Pam3CSK4, a TLR2 ligand). Pre-treatment of murine RAW 264.7 and human THP-1 macrophages with noscapine analogs (50 µM) for 4 hr followed by a 12 hr stimulation with the TLR4-MD-2 ligand meningococcal LPS (doses 10-0.31 pM) resulted in a significant reduction in nitric oxide and TNFα release compared to cells that were treated with DMSO (untreated control) and stimulated with LPS or Pam3CSK4 (FIG. 1). Similar reduction in nitric oxide and TNFα release was observed in time-course of drug pre-treatment i.e. 1, 2 and 12 hrs. Noscapine analogs displayed significantly higher anti-inflammatory activity compared to the parent drug noscapine. Similarly, co-treatment of human THP-1 and murine RAW 264.7 macrophages with noscapine analogs and TLR-ligands LPS and Pam3CSK4 for 12 hr resulted in significant reduction of TNFα and nitric oxide release (FIG. 2). However, no effects on cell viability as determined using trypan blue vital dye exclusion, microscopic morphology and LDH release were observed in these studies. THP-1 cells incubated for 48 hr with 50 µM of either DMSO, Nos, Br-nos or Rd-Br-nos released 5, 7, 8 and 10 IU/L of LDH, respectively. Noscapine or noscapine analogs alone did not induce inflammatory responses or impair cellular viability in human or murine macrophages. The noscapine analogs dampened TLR-mediated TNFα and nitric oxide (NO) release from human and murine macrophages in a dose-dependent manner (FIG. 3). In summary, these data demonstrated significant innate immune anti-inflammatory activity of noscapine analogs to TLR ligands compared to untreated controls or the parent drug noscapine.

Anti-Inflammatory Potential of Noscapines in Sterile Inflammation

Figure 4:
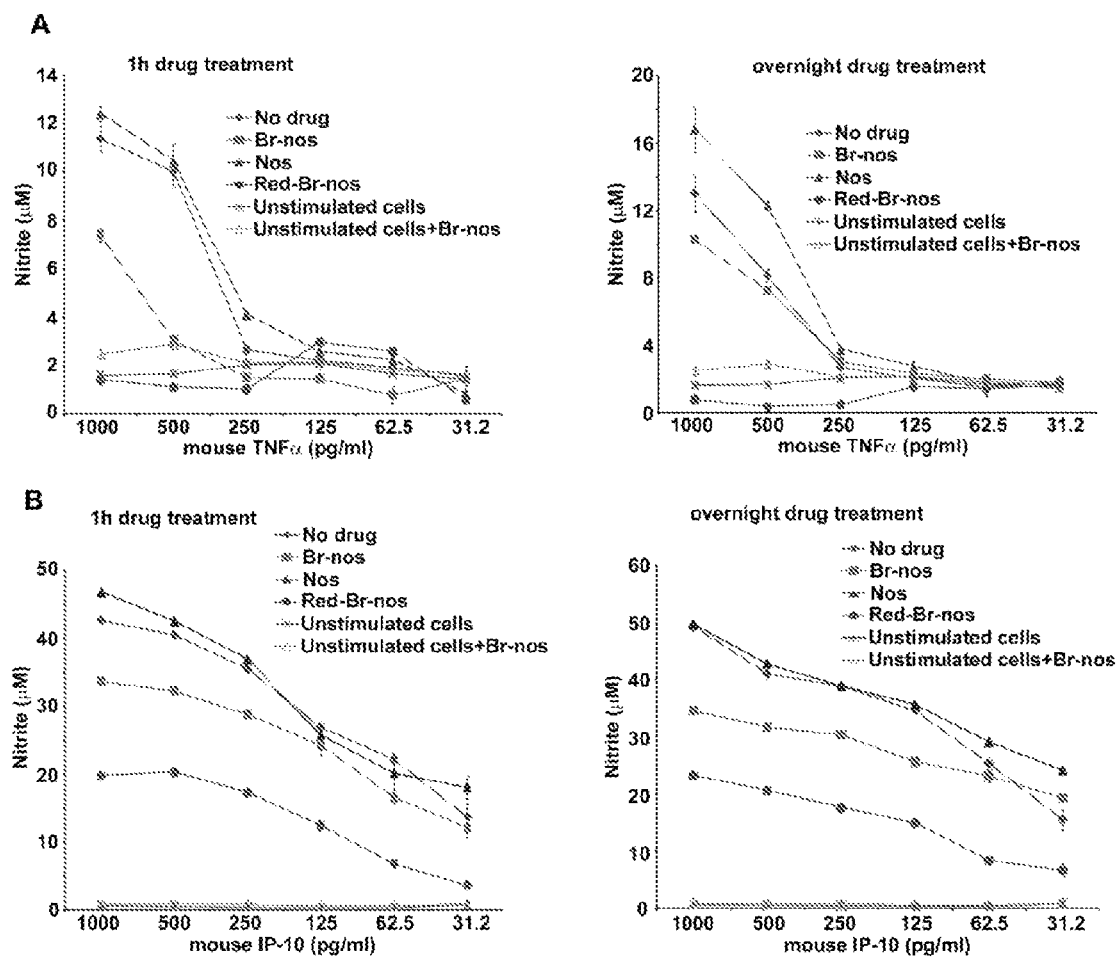
FIG. 4 illustrates noscapine analogs dampen sterile inflammation. Panel A shows ScCr (TLR4-deficient) cells, and panel B shows RAW264 (TLR4-sufficient) cells, both were treated with 50 μM noscapine analogs for 1 hr (left panel) or overnight (right panel) then stimulated with the murine chemokine IP-10 (CXCL10) or the murine cytokine TNFα in concentrations from 1000-31.2 pg/ml and incubated overnight. NO release was measured in supernatants by the Griess method. No drug refers to ScCr cells treated with DMSO and stimulated with murine cytokine TNFα (panel A); RAW 264.7 cells stimulated with murine chemokine IP-10 (panel B). Nos refers to noscapine and non-TLR ligands TNFα (panel A) or IP-10 (panel B). Br-nos refers to 9-bromonoscapine and non-TLR ligands. Red-Br-nos refers to Reduced bromonoscapine and non-TLR ligands. Unstimulated cells were used as control and were treated either with DMSO only or Br-nos (50 μM). Error bars represent SD from mean of at least duplicate readings. p values were calculated with reference to no drug values and were <0.0001 for Br-nos and Red-Br-nos drug treatment and not significant for the parent drug noscapine.

The anti-inflammatory role of brominated noscapines was also confirmed in a sterile inflammation model mimicked by macrophages stimulated with recombinant cytokines and chemokines instead of TLR ligands. Human and murine macrophages as well as HEK-TLR transfected cells were induced with non-TLR ligands such as the cytokine TNFα or the chemokine IP-10/CXCL10. Noscapine analogs reduced nitric oxide release from murine macrophages ScCr (TLR4-deficient cells) stimulated with recombinant cytokine mouse TNFα (FIG. 4, Panel A). Furthermore, noscapine analogs significantly decreased nitric oxide release from murine RAW 264.7 (TLR4-sufficient cells) macrophages induced with recombinant mouse chemokine IP-10/CXCL10 (FIG. 4, Panel B).

Noscapine Analogs do not Bind TLR-4-MD-2 Receptor

Figure 5:
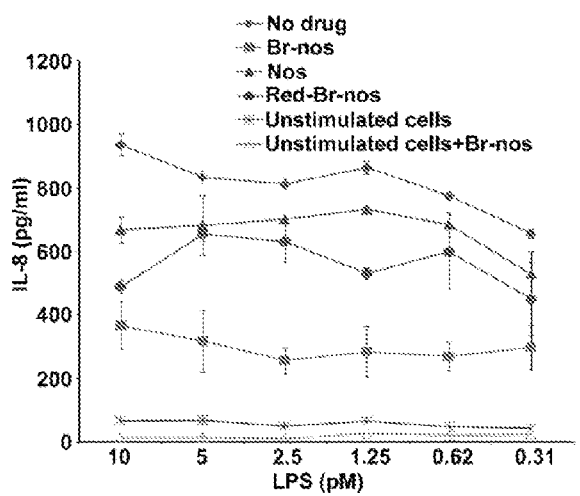
FIG. 5 illustrates noscapine analogs dampen TLR-mediated IL-8 release. HEK293 cells stably transfected with human TLR4-MD-2-CD14 receptors were co-treated with 50 μM of noscapine analogs and LPS concentrations ranging from 10-0.31 pM and incubated overnight. IL-8 release in supernatants was determined by ELISA. No drug: RAW264.7 cells treated with DMSO (50 μM) alone followed by LPS or Pam3CSK4 induction. Nos: noscapine and the TLR ligand. Br-nos: 9-bromonoscapine and the TLR ligand. Red-Br-nos: Reduced bromonoscapine and the TLR ligand. Unstimulated cells were used as control and were treated either with DMSO only or Br-nos (50 μM) without the TLR ligand, and p values were calculated with reference to no drug values and were <0.0001 for Nos, Br-nos and Red-Br-nos drug treatment.

To confirm the anti-inflammatory effects of noscapine analogs, HEK293 human epithelial cells stably-transfected with TLR4-MD-2-CD14 receptors were co-treated with noscapine analogs (50 µM) and varying LPS concentration followed by overnight incubation. Noscapine analogs significantly reduced TLR4-MD-2 mediated IL-8 release from HEK/TLR4-MD-2-CD14 cells (FIG. 5). These drugs also significantly reduced IL-8 release by ~3 fold (no drug=1400 pg/ml, Br-nos=650 pg/ml, Red-Br-nos=400 pg/ml) from HEK293 cells transfected with TLR2 alone or TLR2/6 receptors induced with Pam3CSK4. Noscapine analogs decreased inflammatory responses induced by both LPS (a TLR4-MD-2 ligand) and by Pam3CSK4 (a TLR2 ligand) suggesting that noscapine analogs did not exert their anti-inflammatory effect by selectively inhibiting TLR4 and TLR2 cell surface receptor dimerization. Unlike paclitaxel that binds human and murine MD-2, the anti-inflammatory role of brominated noscapines appeared to be due to effects on tubulin dynamics.

Red-Br-Nos Induces Robust Autophagy in Human Macrophage Cells

Figure 6:
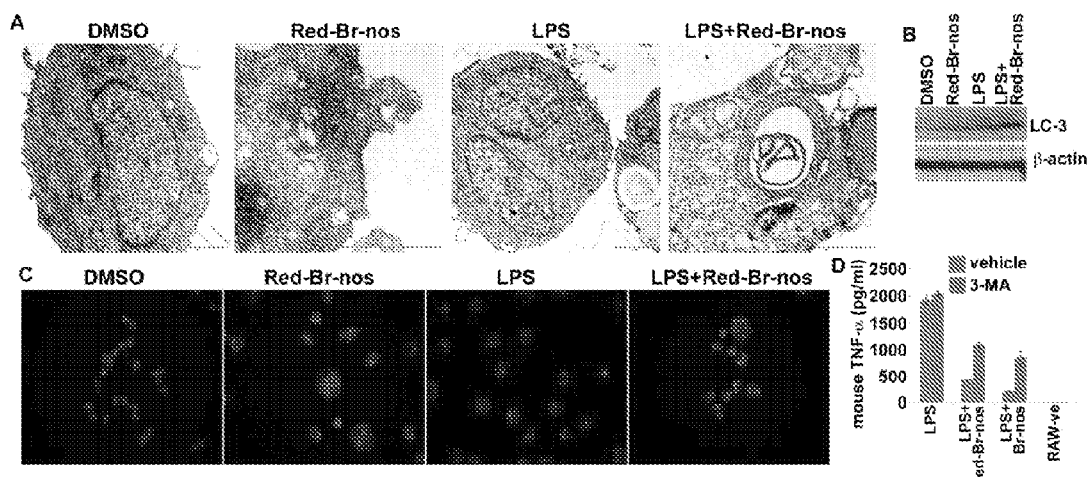
FIG. 6 illustrates noscapine analogs induce autophagy in human macrophages. Panel A shows representative electron micrographs of human macrophage cells THP-1 treated overnight with LPS alone (2 pM concentration) or LPS and reduced bromonoscapine (50 μM). Drug induced autophagy was noted with increased vacuolation in the cytoplasm. Panel B illustrates Western blot of autophagy marker LC3 protein in cell pellets shown in panel A. Panel C shows fluorescence microscopic analysis of THP-1 cells treated for 24 hrs with DMSO (control), Red-Br-nos, LPS, Red-Br-nos and LPS followed by staining with 1 μg/ml acridine. Note the formation (red fluorescence) of acridine orange-accumulating acidic vesicular organelles (AVOs) in Red-Br-nos treated cells. Panel D shows mouse TNFα release from RAW264.7 cells treated with the autophagy inhibitor 3-MA (50 μM) prior to stimulation with LPS alone or with 50 μM of Red-Br-nos, Br-nos or Nos. TNFα was measured by ELISA. The data represent two independent experiments. p values were calculated with reference to no 3-MA inhibitor and were <0.001 for Nos, Br-nos and Red-Br-nos drug treatment and LPS stimulation.

The brominated noscapine analogs displayed innate anti-inflammatory activity with no effect on cellular viability. However, the underlying mechanism of the exerted anti-inflammatory activity is not known. Autophagy plays an essential role in cellular homeostasis and host defense and it is becoming evident that TLRs are the environmental sensors for autophagy associated with innate immunity. Thus, drug-induced autophagy was investigated as a possible underlying mechanism of the anti-inflammatory effects of noscapine analogs. Electron microscopy data showed that noscapine analogs induced extensive autophagy-related vacuolation in human macrophages THP-1 (FIG. 6A). This drug-induced autophagy was also confirmed by immunoblotting for microtubule-associated protein light chain 3 (LC-3), a well known marker for autophagy. The results demonstrate the conversion of LC3-I, the cytoplasmic form of LC-3, into LC3-II that incorporates into the autophagic membrane (FIG. 6B). Detection of acidic vesicular organelles (AVOs) in THP-1 cells treated with Red-Br-nos further confirmed the drug-induced autophagic activity (FIG. 6C). Further, when autophagy was inhibited by the pharmacological inhibitor 3-MA, a reduction in anti-inflammatory activity exerted by noscapine analogs was observed. Murine RAW264.7 macrophages treated with 3-MA prior to stimulation with LPS and noscapine analogs released more TNFα compared to macrophages without the autophagy inhibitor, 3-MA (FIG. 6D). These data suggest that autophagic clearance mechanisms might be responsible for either dissipating the cytosolic inflammatory signaling complex before it reaches the nucleus to induce pro-inflammatory gene expression or might slow down/decrease protein synthesis leading to reduced release of pro-inflammatory mediators.

Noscapine Analogs Enhance ROS Release in Macrophages

Figure 7:
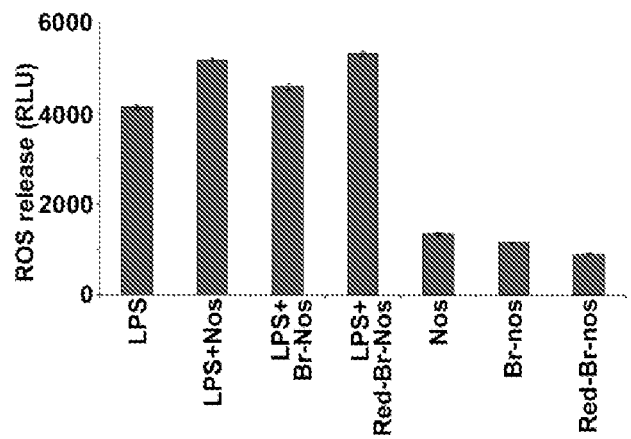
FIG. 7 illustrates Noscapine analogs enhance ROS release. ROS release from THP-1 macrophages was primed with LPS (1 pM) overnight. Noscapine analogs (50 μM) were added just prior to a respiratory burst triggered with PMA (1 μM). ROS release was detected with the chemiluminescent probe lucigenin. p values were calculated with reference to no drug but LPS treated cells and were <0.002.

Oxidative and respiratory burst are vital cellular functions that play an important role in homeostasis and host defense. Oxidative burst leads to the release of highly reactive oxygen species (ROS) radicals. We have previously shown that brominated noscapine analog induces a mitochondrially-driven intrinsic apoptotic cascade by dissipation of the mitochondrial membrane potential. Aneja et al. (2006) Blood 107: 2486-2492, Aneja et al. (2008) Cancer Res 68: 1495-1503. Since changes in mitochondrial membrane potential are usually associated with increases in ROS release, the effects of brominated noscapine analogs on ROS release from LPS-primed human macrophages were investigated using an enhanced chemiluminescence method. The results showed that both noscapine and its brominated analogs enhanced ROS release in LPS primed cells when added just prior to triggering the respiratory burst, but not in unprimed macrophages (FIG. 7). In contrast, no change in ROS release was seen when noscapine or its analogs were added to primed macrophages 2 hr prior to triggering the respiratory burst (data not shown). The data suggest that the enhanced ROS release from primed macrophages may perhaps be due to effects of the drug on mitochondrial membrane potential rather than cellular signaling and macrophage priming.

The invention claimed is:

1. A method of treating Crohn's disease or inflammatory bowel disease (IBD) comprising administering an effective amount of noscapine or a noscapine analog or salt thereof to a subject in need thereof wherein the noscapine analog is a compound comprising Formula A:

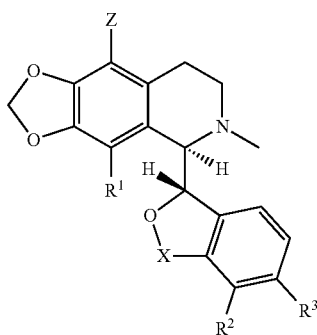

Formula A or pharmaceutically acceptable salts, prodrugs or derivatives thereof;

wherein Z is a halogen, nitro, or nitrogen wherein nitrogen may be optionally substituted with $R^4$;

X is carbonyl or methylene ($CH_2$) optionally substituted with $R^4$;

$R^1$, $R^2$, and $R^3$ are each independently an alkoxy optionally substituted with one or more $R^4$;

$R^4$ is independently selected from alkyl, alkenyl, alkanoyl, halogen, nitro, cyano, hydroxy, amino, mercapto, formyl, carboxy, carbamoyl, alkoxy, alkylthio, alkylamino, dialkylamino, alkylsulfinyl, alkylsulfonyl, arylsulfonyl, carbocyclyl, aryl, and heterocyclyl wherein $R^4$ is optionally substituted with $R^5$;

$R^5$ is selected from halogen, nitro, cyano, hydroxy, trifluoromethoxy, trifluoromethyl, amino, formyl, carboxy, carbamoyl, mercapto, sulfamoyl, methyl, ethyl, propyl, tert-butyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, and heterocyclyl.

2. The method of claim 1, wherein $R^1$, $R^2$, and $R^3$ are each methoxy.

3. The method of claim 1, wherein Z is halogen.

4. The method of claim 1, wherein the noscapine analog is selected from 9-bromonoscapine, 9-chlornoscapine, and 9-aminonoscapine.

* * * * *